United States Patent [19]  [11] Patent Number: 4,619,786
Henniger et al.  [45] Date of Patent: Oct. 28, 1986

[54] PREPARATION OF 6-α-BROMO- AND/OR 6,6-DIBROMO-PENICILLANIC ACID-1,1-DIOXIDES

[75] Inventors: Peter W. Henniger, Leiden; Johannes K. van der Drift, Delft, both of Netherlands

[73] Assignee: Gist-Brocades N.V., Delft, Netherlands

[21] Appl. No.: 486,981

[22] Filed: Apr. 19, 1983

[30] Foreign Application Priority Data

Apr. 19, 1982 [GB] United Kingdom ............. 8211301

[51] Int. Cl.$^4$ ............... C07D 499/00; A61K 31/425
[52] U.S. Cl. .................................................. 540/310
[58] Field of Search ............... 260/245.2 R; 424/270

[56] References Cited

U.S. PATENT DOCUMENTS 4,432,970  2/1984  Kellogg .................. 260/245.2 R
4,444,687  4/1984  Gottstein .................. 260/245.2 R

FOREIGN PATENT DOCUMENTS 0002927 11/1979 European Pat. Off. .
0030771  4/1983 European Pat. Off. .
2000138A 11/1979 United Kingdom .
2045755A 11/1980 United Kingdom .

OTHER PUBLICATIONS

Clayton et al., J. Chem. Soc. (London), 1969, pp. 2123–2127.
Cignarella et al., J. of Org. Chem., vol. 27, pp. 2668–2669, (1962).

*Primary Examiner*—Nicholas S. Rizzo
*Attorney, Agent, or Firm*—Bierman, Peroff & Muserlian

[57] ABSTRACT

A process for the preparation of at least one compound of a formula selected from the group consisting of and their salts and esters wherein X is selected from the group consisting of hydrogen and a substituent such as halogen and acetoxy comprising diazotizing a compound of the formula and salts and esters thereof wherein X has the above definition and brominating the resulting diazotized compound with at least an equimolar amount of a nitrosating agent in the presence of 1 to 5 equivalents of a strong acid in solution or suspension in a mixture of water and an at least partially water-miscible organic solvent with the amount of water being 1 to 20% by volume containing at least equimolar amounts of hydrogen bromide and bromine which bromo compounds are useful intermediates for the preparation of penicillanic acid-1,1-dioxide and its derivatives and novel 6-diazo-intermediates.

21 Claims, No Drawings

PREPARATION OF 6-α-BROMO- AND/OR 6,6-DIBROMO-PENICILLANIC ACID-1,1-DIOXIDES

STATE OF THE ART

Netherlands patent application Ser. No. 80-01285 describes the preparation of 6-α-bromo-penicillanic acid of the formula

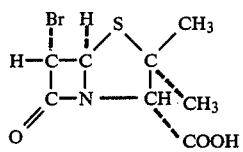

by diazotization of 6-β-amino-penicillanic acid of the formula

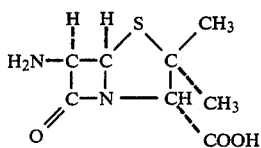

hereinafter referred to for brevity as 6-APA with an alkali metal nitrite, for example sodium nitrite, in the presence of sulfuric acid and a large excess of a bromide anion donor, for example sodium bromide.

It is to be observed that the diazotization-bromination method of Cignarella et al also produces, as was to be expected by persons skilled in the art, in relatively minor amounts the compound 6,6-dibromo-penicillanic acid of the formula

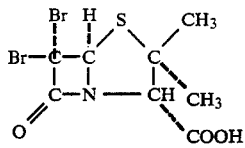

a fact brought out by the confirmatory experiments conducted by Clayton [J. Chem. Soc. (C), 2123 (1969)]. Use of the Cignarella method also gives rise, according to experimentation, to 6-hydroxy-penicillanic acid and to one of the two possible isomers of 6-bromo-6-hydroxy-penicillanic acid of the formulae

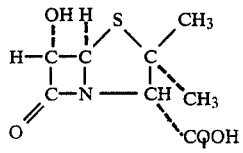 and 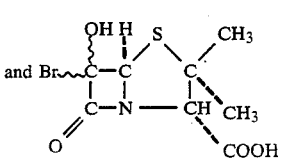

VII                VIII

The generation of these compounds is difficult to minimize in attempts to improve the diazotiazation-bromination procedure of Cignarella and a considerable amount of degradation products also occur. It is possible to separate out in an almost selective fashion the useful reaction products, i.e. all of the monobromide of formula IV and most of the dibromide of formula VI, by performing the reaction in the presence of a water-immiscible solvent, preferably dichloromethane, followed by extraction with dichloromethane, etc. However, it has been found that the Cignarella-method, though more or less useful on a small laboratory scale, is not suited for production on an industrial scale for the following reasons. First, due to the poor solubility of 6-APA, the reaction has to be performed in fairly high dilution. Second, the conversion produces so much heat that even on a scale of only about 0.5 mole of 6-APA, cooling with ice-salt mixtures is barely sufficient to keep the temperature under control and at the same time to ensure a fast conversion and stability of the compounds of formulae IV and VI at low pH in the presence of much water. Third, the already mentioned instability of the useful products at a pH of about 0.5 prohibits prolonged reaction times and extraction procedures as well as stirring times, features associated with production on an industrial scale. This effect was already noticeable on a laboratory scale going from 0.1 to 1 mole scale conversions.

Netherlands Patent Application No. 80-01285 also describes the use of a variation of another diazotization-bromination procedure for 6-APA which was published by Clayton [J. Chem. Soc. (C), 2123 (1969)]: henceforth called the Clayton procedure which uses bromine instead of sodium bromide. The original Clayton procedure, producing mainly the dibromide of formula VI, may in practice give a greater amount of useful product as compared with the Cignarella procedure. This method is again associated with the production of a very substantial amount of heat, and involves indadequate simultaneous addition of bromine and nitrite to the very acidic solution of 6-amino-penicillanic acid.

The variation of the Clayton procedure employed in Netherlands Patent Application No. 80-01285 involves slow portion-wise addition of 6-amino-penicillanic acid to a mixture of bromine, sodium nitrite, sulfuric acid, dichloromethane and water. However, use on a commercial scale of this variant is questionable in view of the substantial amount of heat generated during the conversion and the requirement of very accurate dosing of 6-amino-penicillanic acid.

The compounds prepared by the process of the invention are valuable intermediates for the synthesis of penicillanic acid-1,1-dioxide compounds of the formula

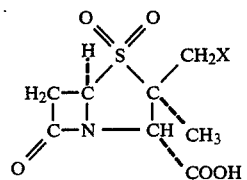

wherein X is as defined above, and salts and esters thereof. If X is hydrogen, the compound is PAS. These compounds have useful pharmacological properties, for example as effective inhibitors of several types of β-lactamases present in various kinds of bacteria.

The compounds of formula III in which X is H and salts and esters thereof were already known from European Patent Application No. 78-300860.0 (Publication No. 0002927). Preparation methods indicated in this application are confined to oxidation by usual methods of 6-APA involving dual protection of the amino group as well as of the carboxy group. Although protection of the carboxy group possibly is not really necessary, protection of the amino group has to be introduced prior to performance of the oxidation reaction. This means two extra separate steps, i.e. protection and deprotection. 6-β-amino-penicillanic acid-1,1-dioxide and its esters when prepared by this route can hardly be considered as attractive starting materials for the desired development of an overall synthesis of compounds of formula IX from which an economic, industrial large scale process can be derived eventually.

Fortunately, in a series of patent applications, e.g. European Patent Application No. 80-201192.4 (Publication No. 0030771), there is described a simple method for the synthesis of 6-β-amino-penicillanic acid-1,1-dioxide and its esters prepared therefrom by conventional methods starting from 1,1-dioxides of penicillins accessible by large scale fermentations such as benzylpenicillin and involves a one-pot conversion of, for example, benzylpenicillin-1,1-dioxide by sequentially protective silylation of the carboxy group in situ, formation of the imide chloride with phosphorous pentachloride and conversion of the imide chloride with preferentially isobutanol to the imino ether, whereupon hydrolysis afforded the desired starting material. The compounds of formula IX in which X is halogen are known from Dutch patent application No. 81-00209.

The compound of formula III in which X is H, hereinafter sometimes referred to for brevity as "amino-PAS", when prepared in such a way in two steps from benzylpenicillin, in principle has the prerequisites of an economically attractive starting material since in the first step benzylpenicillin-1,1-dioxide is obtainable on a large scale in 70-90% yields by simple and straightforward oxidation with permanganate. The feasibility of using, for example, the compound amino-PAS or a derivative in which X is not H but a substituent and esters thereof as an economically possibly attractive point of departure being indicated, it then depended whether or not these starting material can be transformed in attractive yields to the compounds of formulae I and/or II. In this connection, development of suitable conditions for diazotization-bromination of 6-β-amino-penicillanic acid-1,1-dioxide was of course necessary.

It was found that upon diazotization of amino-PAS in the presence of bromine according to the Clayton procedure, very small amounts of mainly the dibromide of formula II (X=H) are formed. Gradual replacement of water by acetonitrile did result in a small increase of the formation of mainly the dibromide, but the yields remained discouragingly low. Diazotization at low pH carried out in the presence of bromine as well as of bromide anions did result occasionally in estimated acutal yields of a maximum of 40-45% of useful products. Such yields were however not reached in a systematic fashion and the obtained products were usually substantially impure.

OBJECTS OF THE INVENTION

It is an object of the invention to provide an improved process for the diazotization of 6-β-amino-penicillanic acid-1,1-dioxide derivatives.

It is another object of the invention to provide novel diazo-intermediate compounds.

These and other objects and advantages of the invention will become obvious from the following detailed description.

THE INVENTION

The novel process of the invention for the preparation of at least one compound of a formula selected from the group consisting of

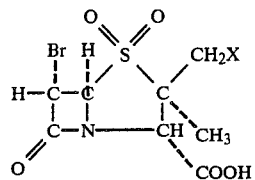

I and

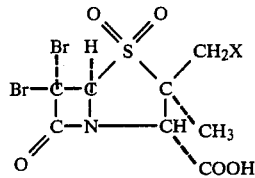

II and their salts and esters wherein X is selected from the group consisting of hydrogen and a substituent such as halogen and acetoxy comprising diazotizing a compound of the formula

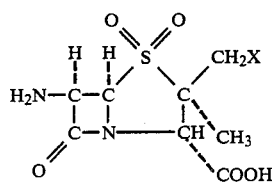

III and salts and esters thereof wherein X has the above definition and brominating the resulting diazotized compound with at least an equimolar amount of a nitrosating agent in the presence of 1 to 5 equivalents of a strong acid in solution or suspension in a mixture of water and an at least partially water-miscible organic solvent with the amount of water being 1 to 20% by volume containing at least equimolar amounts of hydrogen bromide and bromine.

A preferred mode of the process comprises diazotization of a 6-β-amino-penicillanic acid-1,1-dioxide derivative of the formula

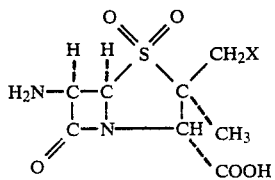

III and salts and esters thereof wherein X is as defined above and subsequently brominating the diazotized compound at a temperature between −20° C. and 30° C., preferably between −10° and 15° C., with at least an equimolar amount of a nitrosating agent in the presence of 1 to 5 equivalents of a strong inorganic or organic acid in solution or suspension of a mixture of water and a partly or completely water-miscible organic solvent medium, the amount of water present being from 1 to 20% by volume, containing hydrogen bromide and bromine in at least equimolar amounts.

Optionally, an auxiliary agent which facilitates the bromination of the diazotized compound can be used in amounts varying from 10% to at least an equimolar amount of the dioxide starting material. As auxiliary agents which optionally can be added to the reaction mixture, various types of organic compounds can be used such as tertiary amines, pyridine-N-oxides, sulfones and sulfoxides and in general amines, ureides and imides, all having adjacent to an acyl fragment a nitrogen-hydrogen fragment, various types of compounds having an imine (C=N—H) type unit, such as 1,1,3,3-tetraalkyl-guanidines, as well as various non-hydroxylic derivatives of malonic acid. However, it will be appreciated that other suitable additives not specifically named in the description of the present invention may be used too.

The auxiliary agents which may optionally be employed in the diazotization procedure of the invention fall into six classes of organic compounds. They are in general tertiary amines, pyridine-N-oxides, sulfones and sulfoxides, and compounds having in a chain or a ring an acylamino group with at least one nitrogen-hydrogen bond (N—H) and compounds having a C=N—H fragment. Within the six classes of auxiliary agents, there is not much restriction with respect to individual structure with the main restriction being that the auxiliary agent should be substantially inert to bromination under the conditions employed. Therefore, most enamines and in general compounds having a towards bromine species highly reactive ethylene or alkyne units are omitted from consideration. Likewise, N,N-dialkyl-aromatic amines which are brominated in the aromatic nucleus very easily are generally not useful. Another conceivable restriction relating to possible nitrosation of a susceptible auxiliary agent leading to an in principle isolatable nitroso-derivative is in the chemical sense hardly of consequence as the amino group of 6-$\beta$-amino-penicillanic acid-1,1-dioxide is much more reactive towards nitrosation.

It will be appreciated that whereas in the description of the invention it is preferred to add the nitrosating agent to the mixture containing the compound of formula II, it is usually equally possible to add proportion-wise the compound of formula II to the mixture containing the nitrosating agent instead. That this latter reversed procedure is in general not preferred is due to health considerations, i.e. unnecessary enhanced danger for possible, permanent or temporary, transformation of certain auxiliary agents into nitroso-derivatives such as N-nitroso amides or imides which may or may not act expediently as nitrosating agents themselves for the compound of formula III.

The reaction conditions of the process of the present invention dedicated to the conversion of 6-$\beta$-amino-penicillanic acid-1,1-dioxide in strongly acidic solution to the compounds of formulae I and II can be described as follows.

While continuously cooling with iced water, the compound of formula II is added with stirring to a mixture consisting of a suitable organic solvent medium, 1–20% by volume of water, preferably 3 to 15% by volume, and 1 to 5 acid equivalents of a strong inorganic or organic acid, preferably an arylsulfonic acid such as p-tolylsulfonic acid, sulfuric acid or hydrobromic acid. Hydrobromic acid and sulfuric acid are introduced preferably as solutions in water, but water present in such solutions as well as the much smaller amounts of water present in the starting material and in commercially available arylsulfonic acids, they are usually sold as hydrates, are accounted for.

The concentration of the compound of formula III in the thus prepared solutions is at least 5% and can be increased to about 10% by a proper choice of the conditions. Subsequently, there are introduced in at least equimolar (to the employed amount of amino-PAS) amounts of hydrogen bromide, optionally an auxiliary agent and at least one equimolar amount of bromine. These agents may be introduced separately, or when possible as a 1:1:1 complex between them (e.g. pyridine hydrobromide perbromide) or as hydrogen bromide and a complex between the auxiliary agent and bromine or as bromine and the salt of the auxiliary agent and hydrogen bromide. At separated or partly separated introduction, it is preferred to introduce bromine or a complex between bromine and the auxiliary agent at the end.

It will be appreciated that when hydrobromic acid is employed to dissolve starting material and to liberate nitroso species from the subsequently introduced nitrosating agent and when at the same time the auxiliary agent is not introduced as a complex with hydrogen bromide, the total calculated amount of hydrogen bromide maybe introduced for sake of simplicity in one portion during the preparation of the solution of the starting material. As soon as a complete or almost complete solution is reached, an at least equimolar amount of the nitrosating agent is introduced at the selected temperature or temperature range. The temperature may vary between $-15°$ and $+25°$ C., preferably between $-5°$ and $+10°$ and more preferably between $0°$ and $+10°$ C.

The nitrosating agent can be a commercially available, cheap alkali metal nitrite, e.g. sodium nitrite, introduced gradually or in a number of approximately equal portions. It is possible, though mostly not preferred, to add dropwise a saturated solution of, for example, sodium nitrite in water while accounting for the amount of water in this solution. The nitrosating agent can also be a commercially available, preferably cheap, cycloalkyl nitrite or alkyl nitrite such as ethyl nitrite, 1-pentyl nitrite, 2-pentyl nitrite, etc., which is added dropwise. The rate of addition of the nitrosating agent will be adjusted to maintain the selected temperature range, but the involved time is usually easily confined to 10 to 30 minutes. The conversion is completed by additional stirring for about 15 to 45 minutes at approximately the same temperature. The final reaction mixture can be treated in various ways, depending on the selected individual conditions of the reaction performed and on the intentions leading to the choice of the selected conditions.

A suitable organic solvent medium means a single organic solvent or a mixture of at least two organic solvents which under the conditions employed do not substantially interfere with the reaction and can take up to about 10% by volume of water or more. Not suitable as single solvents are ketones as they inter-react with diazotized species and various alcohols. Preferred single solvents therefore are inter alia ethyl acetate, methyl acetate, nitromethane, dioxane, tetrahydrofuran, 1,2-dimethoxy-ethane and acetonitrile, all of them having a relatively low boiling point and characterized by easy removal at the end of the reaction in one way or the other. In general the preferred solvent is acetonitrile with as close second best 1,2-dimethoxy-ethane. Depending on the precise conditions of the reaction, one or more of the other solvents indicated above may occasionally represent a proper choice, but acetonitrile closely followed by 1,2-dimethoxy-ethane are nearly always as suitable as any of the other solvents.

Although 1,2-dimethoxy-ethane and particularly acetonitrile can be removed and to a large extent recovered easily and quickly by concentration of the final reaction mixture in vacuo, these particularly good solvents may become objectionable as health and environment regulations become more and more strict in some countries. It was therefore investigated whether these good solvents could be replaced in general by a combination of at least 80% by volume of a common, less objectionable solvent, easily retrievable by separation of layers during the isolation procedure such as dichloromethane and in particular ethyl acetate, and of at most 20% by volume of a dipolar aprotic solvent which increases dissolution of water and salts, but which often cannot be recovered easily. Good solvents of this nature are 1,1,3,3-tetramethylurea but in particular dimethyl sulfoxide, tetrahydrothiophene-1,1-dioxide (sulfolane), and a class of non-hydroxylic solvents structurally derived from malonic acid wherein the carboxylic radicals are esterified by lower alkyl groups or replaced by a cyano group, e.g. dicyanomethane, ethyl cyanoacetate, diethyl malonate, which three solvent types in addition act as auxiliary agent themselves. Less suitable appeared to be the most common fully N-alkylated amide type solvents such as dimethylacetamide and N-methylpyrrolidin-2-one.

The relative amount of water in the diazotization bromination mixture is usually between 1 and 20%, preferably 3 to 15%, by volume. It is not possible to define in a more precise way the optimum relative amount of water as this varies from case to case and depends on a number of selected reaction conditions such as the nature of the organic solvent medium, the nature of the employed strong acid, the nature of the nitrosation agent and the nature of a possibly applied auxiliary agent.

While other strong acids, i.e. strong organic acids, can be used occasionally to dissolve amino-PAS or its derivatives and to furnish a sufficiently acidic solution, in general the most appropriate acids are aryl sulfonic acids, sulfuric acid and hydrobromic acid, and especially the last mentioned acid. In this connection, it is to be noted that phosphoric acid is not well-applicable. An amount of 1 to 5 acid equivalents has been mentioned before but relatively good results are usually obtained with about 1.5 or more acid equivalents.

The intrinsic versatility of the diazotization-bromination sequence involving an intermediate diazonium-derivative does not make possible a more precise delimitation of the necessary amount of strong acid for the general case, as under otherwise identical conditions, reactions involving cycloalkyl nitrites and alkyl nitrites need up to about one acid equivalent more of the strong acid than the same conversions employing, for example, sodium nitrite.

As an alternative embodiment of the process of the present invention, the overall yields have been found to be improved additionally by the use of an auxiliary agent in certain cases.

One of the inherent aspects of diazotization-bromination of 6-$\beta$-amino-penicillanic acid-1,1-dioxide under conditions involving a diazonium-intermediate is then, that by the same overall process, but in a separate fashion the dibromide of formula II as well as the monobromide of formula I can be prepared by diversification in the ratios of hydrobromic acid, bromine, the starting material of formula III and the possible use of a properly chosen auxiliary agent. However, even with only in mind application of the process towards a synthesis of PAS, the following examples in the strict sense do not allow for a reliable effective classification of the auxiliary agents since yield is not simply a matter of the identity of the auxiliary agent. Each auxiliary agent requires its own most appropriate conditions so that an absolute difference in actual yield of 20% between two agents, e.g. 70% versus 50%, whether or not reached in otherwise identical conditions, does not necessarily indicate that the same difference will prevail after determination of the most appropriate conditions for each of both auxiliary agents. It may be larger or smaller, though such a great difference is not unlikely an indication that the first agent is more effective but not by how much. In an industrial process according to the present invention, the choice of the most suitable auxiliary agent will not only relate to yield and price of the agent, but also to ecological aspects and to ease of manipulation, favoring auxiliary agents which are not extracted or easily removed by washing of the organic solvent extracts such as in general tertiary amines, pyridine-1-oxides, hydantoin or succinimide, or which are fully recovered by extraction at neutral pH such as for instance caprolactam.

In view of the economic applicability of the invention, the auxiliary agents optionally used in the process of the invention are those which, for example, in acetonitrile and together with bromine employed in about 50% excess, produce the compounds of formula I and/or II in estimated actual conversion yields of at least 65%. Suitable auxiliary agents which may be used within the invention in certain specific situations are:

(a) Tertiary (cyclo) aliphatic amines having attached to the nitrogen atom three groups selected from straight or branched-chain alkyls containing up to 6 carbon atoms and from saturated 5 to 7 membered cycloalkyl groups;

(b) Tertiary saturated 5 to 7 membered heterocyclic amines, the ring nitrogen being further attached to a (cyclo)alkyl group as defined above, while the ring may incorporate one oxygen atom or one further nitrogen atom carrying a (cyclo)alkyl group as defined above, e.g. N-ethylpyrrolidine, N-ethyl-piperidine, N-methyl-morpholine or N,N'-dimethyl-piperazine;

(c) Tertiary, fully unsaturated heterocyclic amines comprising pyridine, quinoline, isoquinoline, pyrimidine, pyrazine, N-(cyclo)alkyl-imidazole, N-vinyl-imidazole, and the (cyclo)alkyls as defined above;

(d) Pyridine-1-oxides;

(e) Sulfones and sulfoxides having attached to the sulfur atom two optionally substituted groups selected from the group consisting of alkyl, cycloalkyl, arylmethyl, arylethyl, aryl or a trimethylene, a tetramethylene or pentamethylene unit, with for aryl phenyl, biphenyl 1- or 2-naphthyl and pyridyl, and the (cyclo)alkyl groups as defined above, such as dimethyl sulfoxide, sulfolane, dimethylsulfone or diphenylsulfoxide;

(f) Alkyl, cycloalkyl, arylmethyl, arylethyl and aryl carbonamides as well as N-mono(cyclo)alkyl and N-monoaryl derivatives thereof, the (cyclo)alkyl and the aryl groups as defined above;
(g) Saturated monocyclic, 5 to 7 membered lactams such as caprolactam;
(h) Alkyl, (cyclo)alkyl, arylmethyl, arylethyl and arylsulfonamides, as well as N-mono(cyclo)alkyl and N-monoaryl derivatives thereof, the (cyclo)alkyl and the aryl groups as defined above;
(i) N-monoacyl-ureides of the formula Q-CO-NH-CO-NH-$Q^1$, wherein Q is a (cyclo)alkyl, arylmethyl, arylethyl or aryl group with the aryl group and the (cyclo) alkyl group as defined above and $Q^1$ is hydrogen or (cyclo) alkyl as defined above, while Q and $Q^1$ can be linked together to form a saturated 5 to 6-membered ring in the methylene or ethylene unit optionally substituted with two methyl groups or one phenyl group, e.g. hydantoin, 5,5-dimethyl-hydantoin, 5-phenyl-hydantoin or N-phenylacetylurea;
(j) Imides of the type $Q^2$-CO-NH-CO-$Q^3$, wherein $Q^2$ and $Q^3$ individually represent (cyclo)alkyl, arylmethyl, aryl ethyl or aryl groups with aryl and (cyclo)alkyl as defined above, while $Q^2$ and $Q^3$ also can be linked together to form a saturated 5 to 6-membered ring optionally substituted in the ethylene or propylene unit by one or two methyl groups or one phenyl group, e.g. N-benzoyl-benzene carbonamide or succinimide;
(k) Disulfonylamines of the type aryl-$SO_2$-NH-$SO_2$—aryl with aryl the same or different and defined as above;
(l) Composite imides of the type aryl-$SO_2$-NH-CO-$Q^4$, wherein $Q^4$ is aryl or (cyclo)alkyl, with aryl groups and the (cyclo)alkyl groups as defined above;
(m) Phthalimide and saccharine;
(n) Guanidine and guanidines carrying up to four lower alkyl groups, having a C=N-H fragment with lower alkyl as defined above, for instance 1,1,3,3-tetramethylguanidine;
(o) Non-hydroxylic derivative of malonic acid in which the carboxyl groups are replaced by two cyano, and/or N,N-di(lower)alkyl-carbamoyl and/or (lower)alkoxycarbonyl groups, optionally substituted in the methylene group by a lower alkyl group, and
(p) $\alpha,\omega$-dicyanoalkanes, e.g. 1,2-dicyanoethane.

With reference to the nitrosating agent, it was found that, while again equimolar amounts of the nitrosating agent already promote substantial conversions in the desired direction, maximum yields are usually reached with an approximately 15 to 40% excess. A substantially greater excess may result in diminished yields and the excess of nitrosating agent should not be greater than the employed excess of bromine.

The reaction mixtures obtained are treated with an excess of bisulfite, e.g. a concentrated solution of sodium metabisulsufite in water to destroy still present oxidative agents such as bromide, whereupon dilute alkali metal hydroxide is added until the intended pH is reached. Further manipulation of the water-diluted reaction mixture depends on the original intentions, which guided the selection of the conditions for the reactions performed. There are in general four possibilities for further treatment, namely treatments a,b,c and d respectively.

Treatment a

If it had been intended to prepare in a selective fashion by properly directed choice of the reaction conditions either the dibromide of formula II or the monobromide of formula I, the mixture is brought to a pH of 6 to 7 followed by removal in vacuo of low-boiling organic solvent, purification of the solution in water by extraction with preferably dichloromethane and subsequent extraction of the desired product with, for example, ethyl acetate at pH 2 to 4. After the usual further manipulation, 6,6-dibromo-penicillanic acid-1,1-dioxide or 6-$\alpha$-bromo-penicillanic acid-1,1-dioxide are obtained in substantially pure form, in the case of the dibromide with yields of 65% or more and in the case of monobromide in yields of at least 50%.

However, when bromides prepared by the invention are only intended as intermediates to produce PAS, one can confine the process for the preparation of crude mixtures of both brominated products and the following variations can be followed.

Treatment b

The simplest method is to adjust the pH of the aqueous solution of the crude product to 2.5 or higher while optionally the low boiling organic solvent is removed.

Treatment c

A somewhat extended route involves removal in vacuo of low boiling solvent at pH 2.5, extraction of the desired products with ethyl acetate at pH 2.5 and washing the combined extracts once with a small volume of a saturated sodium chloride solution in water and mixing the combined extract with water.

Treatment d

With this method, reaction mixtures are treated, usually carried out to compare the effects of variations of the reaction conditions on the yield of the desired brominated products, closely following treatment a. The finally obtained combined extract is washed with saturated sodium chloride solution, dried over an anhydrous inorganic salt, filtered and evaporated followed by drying in vacuo. The purifying extraction with dichloromethane at approximately neutral pH can be omitted when the employed conditions are known to give relatively good yields and the auxiliary agent employed is not extracted at pH 2 to 4 with, for example, ethyl acetate.

In particular, associated with mixed products obtained by treatment d is a semi-quantitative estimation of the combined yield of the compounds of formulae I and II. A purely theoretical maximum yield is calculated from the integrals of well separated absorption lines in the PMR spectrum. Accounted for are the ratio between dibromide and monobromide and also recognizable known impurities due to remaining solvent, often only ethyl acetate, to sometimes remaining auxiliary agent and to occasionally water.

The estimated actual conversion yield is therefore a qualitative approximation based on an overall impression of the spectrum. The difference between the maximum yield and the actual yield is therefore related to quality indications as excellent, very good, good and reasonable. By taking PMR spectrum of mixures of a weighed amount of isolated product and a weighed amount of a reference compound, i.e. 3,4,5-trimethyoxypenylacetic acid, it was found repeatedly that the real conversion yield was always at least 90% of the estimated actual yield. On the average, occasionally too high estimation of the actual yield is compensated by consistently ignoring the water content of the starting material of formula III (6 to 7% by weight).

The above described method for the conversion by diazotization-bromination of 6-β-amino-penicillanic acid-1,1-dioxide into the compounds of formulae II and/or I characterized by relatively mild and versatile conditions involving generation of a diazonium intermediate is in principle also relatively well-applicable to esters of amino-PAS. The esters of compounds of formulae I and II, especially those of formula II, isolatable from such conversions, are however more conveniently prepared by the related process described hereafter, involving as intermediates novel 6-diazo-intermediates since the very mild conditions of this second process of the present invention are more in harmony with the fragile nature of the ester groups involved.

The hereinbefore described diazotiszation-bromination process of the invention has so far been particularly described with respect to amino-PAS. However, it can be applied also to other related compounds which are embraced by formula III, and especially those wherein no esters or salts of III are used.

A second aspect of the present invention involves the novel intermediate 6-diazo-penicillanic acid-1,1-dioxide derivatives of the formula

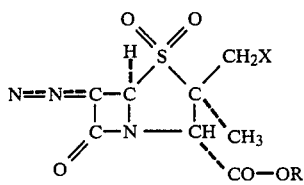

wherein X is defined above and R is hydrogen or an ester radical or salts thereof and their preparation. Such diazo compounds can be isolated and thereafter preserved as they are thermally stable enough under appropriate storage conditions and subsequently at a desired moment amenable to various operations, such as bromination to compounds of formula I and/or II.

It will be appreciated that the compounds of formula X per se and salts thereof as well as methods for their preparation and isolation consitute an important and separate feature of the present invention. It serves as another independent indication that on diazotization the compounds of formula III behave in a surprisingly and unexpectedly different way as compared with 6-APA and corresponding derivatives as 6-diazo-penicillanic acid has hitherto not been isolated, nor has it been submitted in crude form to successive reactions.

This aspect of the invention will be particularly described hereafter by reference to the diazo compounds of formula X wherein X and R are both hydrogen. The compound of formula X wherein X and R are hydrogen is prepared in a simple way by dropwise addition of an at least equimolar amount of a preferentially commercially available cycloalkyl nitrile or alkyl nitrite to a suspension of the compound of formula III wherein R is hydrogen in a suitable organic solvent whereby the relatively strongly acidic carboxyl of the starting compound furnishes the required catalysis for the reaction between the nitrite of the nitrostating agent and the amino of the substrate. The nearly quantitative conversion into the 6-diazo derivative of formula X wherein X and R are hydrogen is seen by complete dissolution of the substrate. The conversion proceeds equally well whether or not the small amounts of water present in the starting compound and in the employed solvent have been removed. It is therefore preferred to work with not previously dried, commercially available, good quality organic solvents and with the relatively stable form of the starting material containing 6 to 7% by weight of water. The reaction temperature may be as high as about 25° C. but it is preferred to use a temperature range between 0° and 10° C.

By customary manipulations, the compounds of formula X wherein X and R are hydrogen can be isolated as such, but it is preferred to obtain this compound as its sodium or potassium salt by subsequent introduction of a corresponding alkali metal salt of a weakly acidic organic compound such as α-ethyl-capronic acid. The isolated products are in crude form since they usually contain variable but small amounts of solvent and/or of a cycloalkanol or alkanol originating from the organic nitrite and/or of, for example, α-ethylcapronic acid. Degradation products are however virtually absent. The true yields can be as high as 70% or more. Whilst hydroxyl solvents such as ethanol and reactive carbonyl solvents such as ketones and aldehydes are not suited for the conversions, the other solvents indicated hereinbefore, e.g. acetonitrile, tetrahydrofuran and dioxane are equally suitable for a very good conversion, although in view of the desired expedient isolation of a salt of 6-diazo-penicillanic acid-1,1-dioxide, manipulations are easier when methyl acetate or ethyl acetate are used as solvent for the conversion.

The conditions for suitable and practical conversions of esters of III into the corresponding 6-diazo-derivatives of formula X are as indicated above except that for a conversion of expedient velocity it is necessary to add a preferentially water-soluble, inert organic compound of sufficient acidity having a $pK_a$ in water of 1.5 to 5.0, for example a preferentially water-soluble carboxylic acid which can be removed completely by one or two washings of the resulting solutions of the compounds of formula X.

The suitable relative amount of the acidic substances introduced preferentially before the addition of the (cyclo)alkyl nitrite depends on the nature of the acidic substance, that is it acidity and this relative amount may therefore range between a few mole percent and one acid equivalent with respect to the amount of the substrate. The organic acid can be as weak as acetic acid, but it is preferred to employ a moderately strong carboxylic acid such as chloroacetic acid or oxalic acid.

The progress of the conversion is checked with thin-layer chromatography or, when the nature of the solvent is compatible by infrared spectroscopy. After complete conversion, the resulting solutions are directly, when the solvent employed is, for example, ethyl acetate, washed once or twice with water containing sufficient salt to operate at approximately −10° C., or are likewise washed after replacement of water-soluble solent for e.g. dichloromethane or ethyl acetate, followed by the usual manipulations. The finally obtained esters of 6-diazo-penicillanic acid-1,1-dioxide of formula X are usually solids, occasionally crystalline. The yields of the crude products are good to very good and the purity of such primary isolate varies between reasonable to good.

The thus obtained diazo compounds of formula X can be employed for conversion to the compounds of formulae I and/or II. In the case where R is hydrogen, bromination usually results in a mixture of both brominated compounds of formulae I and II. In the case of esters however, bromination usually produces the monobromides of formula I wherein R is an ester residue almost with exclusion of esters of the dibromides of formula II, or the dibromides of formula II almost by exclusion of the corresponding monobromides of formula I, depending on whether or not the carboxylic acid employed in the preparation of the intermediates of formula X was removed by washing with water or left in the solution containing the intermediates of formula X, inherently indicating an additional and solitary feature of this part of the present invention, in that esters of 6-diazo-penicillanic acid-1,1-dioxide are amendable to the preparation of pure esters of 6-bromo-penicillanic acid 1,1-dioxide or of 6,6-dibromo-penicillanic acid-1,1-dioxide.

Whereas the isolated diazo-derivatives of formula X can be employed to prepare the compounds of formulae I and/or II, it is of course usually preferred to employ in situ preparations of the diazo-derivatives. When R is hydrogen, there is one way of operation and when R is an ester, there are two possible ways of operation.

When R is hydrogen, bromine and hydrobromic acid are always introduced after in situ generation of 6-diazo-penicillanic acid-1,1-dioxide. For these preparations, carried out in situ, the organic solvent is preferentially acetonitrile, 1,1-dimethoxyethane or for example, ethyl acetate combined with at most 20% by volume of sulfolane, dimethyl sulfoxide, tetramethyl-urea or a non-hydroxyl derivative of malonic acid as hereinbefore defined.

The compounds of formulae I and II are valuable because they can be debrominated to yield penicillanic acid-1,1-dioxide and derivatives thereof which are useful $\beta$-lactamase inhibitors. The debromination step to convert the substances of this application into the $\beta$-lactamase inhibitors is disclosed in U.S. patent application Ser. No. 486,403 file on even date herewith entitled NOVEL PROCESS wherein the said compounds are debrominated by reaction in an aqueous medium with zinc and an acid with a $pK_a$-value measured in water of less than 3.5.

In the following examples there are described several preferred embodiments to illustrate the invention. However, it should be understood that the invention is not intended to be limited to the specific embodiments.

EXAMPLE 1

Crude mixture of 6,6-dibromo-penicillanic acid-1,1-dioxide and 6-$\alpha$-bromo-penicillanic acid-1,1-dioxide a. 2.9 ml of concentrated sulfuric acid were added carefully to 25 ml of iced water and 3 ml of the thus prepared dilute sulfuric acid were added to 30 ml of acetonitrile at 0° to 5° C. The amount of sulfuric acid employed was therefore about 10.5 mmol or 21 acid equivalent. Continuously operating at temperatures between 0° and 5° C., 2.0 g (assumed to be equivalent to 8.0 mmol; in actual fact, only about 7.5 mmol) of 6-$\beta$-amino-penicillanic acid-1,1-dioxide were introduced with stirring which did not result in a complete dissolution and then 8 g (25 mmol) of pyridine hydrobromide perbromide ($C_5H_5N.HBr_3$) were added thereto resulting immediately in a clear solution. 660 mg of sodium nitrite (9.5 mmol) were introduced in five equal portions over a period of about 15 minutes, followed by additional stirring for 30 minutes and then a solution of 1 g of sodium metabisulfite in 20 ml of water was added with stirring whereupon the pH was increased to 5.0 by careful addition of 4N sodium hydroxide. Acetonitrile was removed azeotropically by concentration at 15 mm Hg over about 10 minutes and the resulting solution was acidified with 4N hydrochloric acid to a pH of 2.0 followed by three extractions with about equal volumes of ethyl acetate. The combined extract was dried over anhydrous magnesium sulfate, filtered and completely evaporated in vacuo and after extensive drying in vacuo, the obtained solid weighed 2.61 g.

According to the PMR spectrum of the product ($d_6$-DMSO, 60 Mc), it contained 6,6-dibromopenicillanic acid-1,1-dioxide, 6-$\alpha$-bromo-penicillanic acid-1,1-dioxide, ethyl acetate and pyridine substance (pyridine itself and/or pyridine .HCl or pyridine .HBr) in 13:1:1.5:3.5 molar ratio. ted ing that pyridine is present as such, the calculamaximum yield is 78.7% of useful products. Taking into consideration the very low level of present degradation products as indicated by the PMR spectrum and by thin-layer chromatography and the possibility that pyridine is present as a salt, the estimated actual yield was about 65-70%.

b. The experiment was repeated in the same way except for one alteration in the isolation procedure. To remove pyridine substances, the ethyl acetate extract containing both bromides was washed twice with a small volume of saturated sodium chloride solution and the obtained mixture of bromides weighed 2.46 g with a dibromide versus monobromide molar ratio of 8:1. Taking care of the small amount of remaining ethyl acetate, the maximum yield was calculated as 78.2% of useful products. In view of the good to very good quality with respect to degradation products, the actual yield could be 70% or better.

c. The experiment was repeated except instead of 25 mmol of the bromination complex, only 12 mmol (3.84 g) were employed which in general constitutes a more appropriate excess. The yield of crude bromide mixture was now 2.39 g of an appreciably less pure product containing, apart from a slight amount of ethyl acetate, the dibromide, the monobromide and one unknown by-product in 75:13:12 molar ratio. Apparently, the reduced amount of hydrobromic acid, as it is largely compensated by pyridine, was in this experiment not enough to compensate for the reduced acidity of the second acid equivalent of sulfuric acid.

EXAMPLE 2

Conversion of 6-$\beta$-amino-penicillanic acid-1,1-dioxide into a mixture of 6,6-dibromo- and 6-$\alpha$-bromo-penicillanic acid-1,1-dioxide Continuously operating between 0° and 8° C. maintained by external cooling with crushed ice and water, 2.0 g of 6-$\beta$-amino-penicillanic acid-1,1-dioxide were added to a stirred solution of 2.0 g (10.5 mmol) of the monohydrate of p-tolyl-sulfonic acid in a mixture of 3 ml of water and 30 ml of acetonitrile resulting in complete dissolution. After dissolution of 8.0 g (25 mmol) of pyridine hydrobromide perbromide in the solution, 660 mg (9.5 mmol) of sodium nitrite were introduced in the manner described in Example 1. The reaction mixture was treated likewise including washing of the extract with concentrated sodium chloride solution to obtain 2.54 g of the desired mixture.

Thin-layer chromatography (TLC) and the PMR spectrum of the isolated product indicated good to very good purity with respect to two unknown degradation products present in small to very small amounts. Neglecting degradation products, the PMR spectrum indicated a 12.5:1:1:1.4 molar ratio between the dibromide, the monobromide, ethyl acetate and acetic acid and the calculated maximum yield was 79.8%. The actual yield was estimated to be about 72% and this was corroborated by reduction with zinc at 0° to 5° C. and a pH varying between 4.2 and 4.7 resulting in an at least 60% overall actual yield of penicillanic acid-1,1-dioxide present in a virtually pure final product.

EXAMPLE 3

Repetition of Example 2 using p-tolyl-sulfonic acid but with some variations (a) The experiment of Example 2 was repeated on the same scale and with the same reaction conditions, but acetonitrile was replaced by the same volume of ethyl acetate. As it was anticipated that the yield and the purity of the crude mixture of bromides would be less good, the solution in water after treatment with bisulfite and removal of ethyl acetate in vacuo was preliminarily extracted at pH 6-6.5 twice with dichloromethane. Also, extraction of the desired product at pH 2.0 with ethyl acetate was to some extent controlled by TLC. The yield of product was 2.17 g of, according to TLC and PMR, reasonably good quality. The ratio between 6,6-dibromo-penicillanic acid-1,1-dioxide and 6-α-bromo-penicillanic acid-1,1-dioxide was now 9:5 indicating that this ratio is also dependent on the nature of the organic solvent employed. Taking into account the ethyl acetate present, the maximum yield was calculated as 61.3%. In view of the relatively greater amount of unknown degradation products present, the actual yield was estimated to be 50–55%.

(b) That bromide anions have to be present to obtain satisfactory yields was established by three experiments wherein hydrobromic acid was omitted while using larger amounts of p-tolyl-sulfonic acid. In the first experiment, there were used 2.0 g of 6-β-amino-penicillanic acid-1,1-dioxide, 4.0 g (21 mmol) p-tolyl-sulfonic acid, 0.95 ml of pyridine (12 mmol), 0.62 ml (12 mmol) of bromine, 660 mg (9.5 mmol) of sodium nitrite, 30 ml of acetonitrile and 3 ml of water. The yield was only 1.03 g and the monobromide was the main product and the estimated actual yield was only about 24%.

In two more experiments, the ingredients were 1.82 g (7.35 mmol) of 6-β-amino-penicillanic acid-1,1-dioxide, 4.18 g (22 mol) of p-tolyl-sulfonic acid, 12 mmol of pyridine and bromine, 9.5 mmol of sodium nitrite, 25 ml of acetonitrile and 2.7 ml of water. With yields of 1.20 g and 1.02 g the results were likewise poor and in both cases, the main product was the monobromide and the estimated actual yields were below 20%.

EXAMPLE 4

Repetition of Example 1(a) under changed conditions (a) In the manner indicated in the previous Examples, a mixture of 2.0 g (8 mmol) of 6-β-amino-penicillanic acid-1,1-dioxide in a mixture of 30 ml of acetonitrile, 3 ml of water and 5.25 mmol of sulfuric acid (10.5 acid equivalent) was treated with 3.84 g (12 mmol) of pyridine hydrobromide perbromide and 660 mg (9.5 mmol) of sodium nitrite. The aqueous layer obtained after the usual manipulations was first somewhat purified by extraction with dichloromethane at pH 6.0 to 6.5 and thereafter extracted at pH 2.0 with ethyl acetate to obtain a yield of product of 2.06 g. Taking into account the ethyl acetate present and the 9:11 molar ratio between the 6,6-dibromo- and the 6-α-bromo-penicillanic acid-1,1-dioxide, the maximum yield was calculated to be 69.6%. In view of the reasonably good quality with respect to unknown degradation products, the actual yield was estimated to be 59–61%.

(b) Using otherwise identical conditions and amounts of agents, experiment (a) was repeated with ethyl acetate as the organic solvent to obtain a yield of 1.87 g with a dibromide/monobromide molar ratio of 9:5. The calculated maximum yield was 61.3% and as the quality of the product was only reasonable, the actual yield was probably not better than about 50%.

EXAMPLE 5

Conversion of 6-β-amino-penicillanic acid-1,1-dioxide into a mixture of 6,6-dibromo- and 6-β-bromo-penicillanic acid-1,1-dioxide (a) 1.2 ml of 47% hydrobromic acid (10.5 mmol) and 1.3 ml of water was added at 0°–5° C. to 25 ml of acetonitrile and addition of 2.0 g (8 mmol) of 6-β-amino-penicillanic acid-1,1-dioxide resulted in a clear solution. Continuously operating at a temperature of below 5° C., 3.84 g (12 mmol) of pyridine hydrobromide perbromide were introduced immediately followed by the addition of 660 mg (9.5 mmol) of sodium nitrite in about five equal portions over the course of about 15 minutes. After additional stirring for 30 minutes, 1 g of sodium metabisulfite in 20 ml of water were added whereupon the pH was raised to 5.0 by careful addition of 4N sodium hydroxide. Acetonitrile was removed by concentration in vacuo and the solution in water was extracted at pH 2 with ethyl acetate. The combined extracts were once washed with a small volume of saturated sodium chloride solution, dried over anhydrous magnesium sulfate and filtered. The filtrate was completely evaporated in vacuo and after drying in vacuo, the yield was 2.27 g of product which was, according to TLC and the PMR spectrum of good to very good quality with respect to the presence of unknown degradation products.

The PMR spectrum indicated a 8:6.5:2.3 molar ratio between the dibromide, the monobromide and ethyl acetate and the isolated product therefore contained 1.325 g (3.388 mmol) of 6,6-dibromo-penicillanic acid-1,1-dioxide and 0.859 g (2.753 mmol) of 6-α-bromo-penicillanic acid-1,1-dioxide for a total of 6.141 mmoles of useful product. The maximum yield is therefore 76.7% and the actual yield was estimated to be at least 70%.

(b) Experiment (a) was repeated with two alterations. While maintaining a 10:1 ratio between acetonitrile and water, the amount of hydrobromic acid was increased to 14.5 mmol, and the solution in water was first somewhat purified by extraction with dichloromethane at pH 6.5 before extraction of useful product at pH 2.0. The qualitatively very good product weighed 2.30 g and the ratio between dibromide and monobromide was 5.8:4. The maximum yield was 77.8% and the estimated actual yield was at least 72%.

(c) Experiment (a) was repeated with 7.68 g (24 mmol) of pyridine hydrobromide perbromide while the isolation procedure was identical with experiment (b).

The isolated product of good to very good quality weighed 2.3 g and the ratio between dibromide and monobromide was 9.7:6. The maximum yield was 76.8% and the estimated actual yield was 68–72%.

EXAMPLE 6

Conversion of 6-β-amino-penicillanic acid-1,1-dioxide into a mixture of 6,6-dibromo- and 6-α-bromo-penicillanic acid-1,1-dioxide (a) Continuously operating at 0°–5° C., 0.62 ml (12 mmol) of bromine were introduced into a solution of 1.82 g (7.35 mmol) of 6-β-amino-penicillanic acid-1,1-dioxide in a mixture of 22.5 ml of acetonitrile, 2.5 ml of dimethyl sulfoxide, 2.5 ml of water and 22 mmol of hydrobromic acid (water and hydrobromic acid added as 2.5 ml of a 4% solution of the acid in water), followed by portionwise introduction of 660 mg of sodium nitrite in the manner described before. The customary procedure for isolation of the product involved purification of the solution in water with dichloromethane at pH 6.5 for a yield of 2.08 g of product which, according to the PMR spectrum, was at least good quality with respect to contamination with unknown degradation products. In the product were present 6,6-dibromo-penicillanic acid-1,1-dioxide, 6-α-bromo-penicillanic acid-1,1-dioxide, ethyl acetate, dimethyl sulfoxide and water in 12.3:1.2:1.3:0.5:4 molar ratio. The maximum yield was calculated to 70.6% and the estimated actual yield was 61 to 63%.

The experiment was repeated was 22.5 ml of ethyl acetate instead of the same volume of acetonitrile and the yield was 1.58 g. The calculated maximum yield was 53.9% with a 12:1.5:1.5:0.5:3 molar ratio of the dibromide, the monobromide, ethyl acetate, dimethyl sulfoxide and water. In view of the excellent quantity of the product with respect to unknown degradation products, the actual yield was estimated at about 50%.

(b) Continuously operating at 0°–5° C., 0.62 ml of bromine were introduced into a solution of 1.91 g (7.7 mmol) of 6-β-amino-penicillanic acid-1,1-dioxide in a mixture of 22.5 ml of ethyl acetate, 2.5 ml of tetrahydrothiophene-1,1-dioxide (sulfolane) and 2.5 ml of a 47% solution of hydrogen bromide in water (equivalent to 22 mmol of hydrobromic acid) followed by portionwise introduction of 660 mg (9.5 mmol) of sodium nitrite in the manner described before. The customary procedure for isolation of product involved purification of the solution in water with dichloromethane at pH 6.5 to obtain a yield of 2.17 g of product which, according to the PMR spectrum was of reasonably good quality with respect to the presence of unknown degradation products. The calculated maximum yield of useful product was 60.7% with a 10:0.6:6:6 molar ratio of the dibromide, the monobromide, sulfolane and water and the actual yield was estimated at 53 to 55%.

(c) This experiment was performed in the same way starting from 2.0 g (8 mmol) of 6-β-amino-penicillanic acid-1,1-dioxide, 0.62 ml (12 mmol) of bromine, 660 mg (9.5 mmol) of sodium nitrite, 22 mmol of hydrogen bromide and 2.5 ml of water (given as 2.5 ml of a 47% aqueous solution of hydrogen bromide) and, as organic solvent, a mixture of 22.5 ml of acetonitrile and 2.5 ml (23.5 mmol) of ethyl cyanoacetate. The isolation procedure was as described under (b) to obtain a yield of 2.40 g of product which, according to the PMR spectrum was of good quality with respect to the presence of unknown degradation products. The calculated maximum yield was 77.0% with a 6:5.5:3.3:7 molar ratio between the dibromide, the monobromide, ethyl acetate and water and the actual yield was estimated at 69 to 71%.

(d) Likewise performed was an experiment using 8 mmol of 6-β-amino-penicillanic acid-1,1-dioxide, 12 mmol of bromine, 2.5 ml of a 47% solution of hydrogen bromide in water (22 mol of HBr), 9.5 mmol of sodium nitrite, 22.5 ml of ethyl acetate and 2.5 ml of ethyl cyanoacetate to obtain a yield of 2.16 g of product with a quality of at least good. Ratio of dibromide, monobromide, ethyl acetate was 10.9:4.6:5.3 and the maximum yield was 67.9%. Estimated actual yield was 60 to 62%.

(e) Likewise performed was an experiment using 8 mmol of 6-β-amino-penicillanic acid-1,1-dioxide, 12 mmol of bromine, 2.5 ml of a 47% solution of hydrogen bromide in water (22 mmol of HBr), 9.5 mmol of sodium nitrite, 22.5 ml of acetonitrile and 2.5 ml of diethyl malonate to obtain a yield of 2.23 g of product with a very good quanlity. Ratio of dibromide, monobromide, ethyl acetate, diethyl malonate was 6.2:6.5:4:1.7. Maximum yield was 69.7% and the estimated actual yield was 64 to 67%.

EXAMPLE 7

Conversions of 6-β-amino-penicillanic acid-1,1-dioxide into a mixture of 6,6-dibromo- and 6-β-bromo-penicillanic acid-1,1-dioxide (a) In the way already described repeatedly, a reaction was carried out using 2.0 g (8 mmol) of 6-β-amino-penicillanic acid-1,1-dioxide, 22 mmol of hydrobromic acid, 200 mg of N-benzoyl-benzene-sulfonamide (about 0.77 mmol), 0.62 ml (12 mmol) of bromine, 660 mg of sodium nitrite (9.5 mmol), 25 ml of acetonitrile and 2.5 ml of water. When isolating the product, the extended procedure including washing of the aqueous layer at pH 6.5 with dichloromethane was followed to obtain a yield of 2.44 g of product which according to the PMR spectrum, was of at least good quality with respect to unknown degradation products. The calculated maximum yield was 72% with a 10.6:2.7:2:1.8 molar ratio between the 6,6-dibromo penicillanic acid-1,1-dioxide, 6-α-bromo-penicillanic acid-1,1-dioxide, ethyl acetate and N-benzoyl-benzenesulfonamide and the actual yield was estimated to be 64 to 67%.

(b) Experiment (a) was repeated but instead of the sulfonamide, 0.2 ml (about 1.88 mmol) of ethyl cyanoacetate was used as auxiliary agent to obtain a yield of 2.45 g of product which, according to the PMR spectrum, was of at least good quality with respect to the presence of unknown degradation products. The calculated maximum yield was 75.8% with a 13.6:2.2:2.3 molar ratio between the dibromide, the monobromide and ethyl acetate and the actual yield was estimated to be 68 to 70%.

EXAMPLE 8

Influence of the nature of the auxiliary agent on the yield of useful products in the diazotization-bromination of 6-β-amino-penicillanic acid-1,1-dioxide and on the ratio between 6,6-dibromo-penicillanic acid-1,1-dioxide and 6-α-bromo-penicillanic acid-1,1-dioxide formed The result of variation of the auxiliary agent is given below in abbreviated form and all reaction mixtures obtained were treated in the same way. After completion of the conversion, dilute sodium bisulfite was added followed by partial neutralization by addition of 4N sodium hydroxide, removal of low-boiling organic solvent, usually acetonitrile, purifying by extraction with dichloromethane at pH 6.0 to 6.5 with the number of extractions dictated by the nature of the auxiliary agent, three extractions of useful products with ethyl acetate at pH 2.0, two washings of the combined acidic extract with a small volume of a saturated solution of sodium chloride in water, drying of the resulting extract over anhydrous magnesium sulfate, filtration, evaporation in vacuo and finally drying in vacuo. The isolated products were submitted to analysis by proton magnetic resonance (PMR) applied on solutions in $d_6$-DMSO at 60 Mc with tetramethylsilane as internal reference. All reactions were performed at 0°–5° C. and nitrosation was always carried out with sodium nitrite added in five about equal portions over the course of about 15 minutes followed by 30 minutes additional stirring.

In the abbreviated Examples are given the amount of 6-β-amino-penicillanic acid-1,1-dioxide (referred to as "amino-PAS") ignoring the presence of water, all the ingredients being in mmol or in volumes, the yield in grams, the molar ratios between known components in the isolated product, the calculated maximum yield in which the presence of unknown degradation products is ignored, the overall quality of the isolated product with respect to these unknown degradation products and the estimated actual yield of useful products. As explained before, the actual yield is appraised on the basis of the maximum yield and the quality of the product apparent from further aspects of the PMR spectrum and thin-layer chromatograms.

(a) reaction in the presence of 2,4,6-trimethylpyridine (collidine)

8 mmol of amino-PAS, 22 mmol of HBr, 12 mmol of collidine, 12 mmol of bromine, 9.5 mmol of $NaNO_2$, 25 ml of acetonitrile and 2.5 ml of water were reacted to obtain a yield of 1.8 g Quality good. Dibromide:monobromide:ethyl acetate ratio of 10.5:4.0:2.7. Maximum yield was 58.4% and estimated actual yield was about 50%.

(b) with 1-methyl-imidazole 8 mmol of amino-PAS, 22 mmol of HBr, 12 mmol of 1-methyl-imidazole, 12 mmol of bromine, 9.5 mmol of $NaNO_2$, 25 ml of acetonitrile and 2.5 ml of water were reacted to obtain a yield of 2.07 g of excellent quality. Dibromide, monobromide, ethyl acetate ratio was 11:7:1.3. Maximum yield was 70.5% and estimated actual yield was at least 67%.

(c) with 1-methyl-imidazole

Experiment (b) was repeated with one variation: instead of 12 mmol of bromine, only 9 mmol were employed to obtain a yield of 2.21 g of reasonable quality. Dibromide:monobromide:ethyl acetate ratio was 1:8.5:10.5. Maximum yield was 66.2% and estimated actual yield was about 55%.

(d) with 1-methyl-imidazole

Experiment (b) was repeated with 25 ml of 1,2-dimethoxyethane as organic solvent and with 11 mmol of $NaNO_2$ instead of 9 mmol to obtain a yield of 2.21 g of reasonably good quality. Dibromide:monobromide:ethyl acetate ratio was 6.5:3.6:1.2. Maximum yield was 73.1% and estimated actual yield was 60–63%.

(1) An experiment on the same scale as (d), but involving the customary amount of $NaNO_2$ (i.d. 9.5 mmol) and only 9 mmol of bromine produced like experiment (c) a less good result: 1.83 g of product of only reasonable quality, maximum yield was 65.7% of almost only the monobromide and actual yield was estimated to be about 50–52%.

(2) An experiment like (d) but involving only 10.5 mmol of HBr produced 1.84 g of product of only modest quality with a dibromide to monobromide ratio of 1:10 and an estimated actual yield of less than 45%. In such experiments, the overall acidity was obviously too low, particularly since 1-methyl-imidazole is not a weak base.

(e) with 3-methyl-pyridine 8 mmol of amino-PAS, 22 mmol of HBr, 12 mmol of 3-methyl-pyridine, 12 mmol of bromine, 9.5 mmol of $NaNO_2$, 25 ml of acetonitrile and 2.5 ml of water were reacted to obtain a yield of 1.98 g of good quality. Dibromide, monobromide, ethyl acetate ratio was 5:8:2. Maximum yield was 69.5% and estimated actual yield was 60–62%.

(f) with 2-dimethylamino-pyridine 8 mmol of amino-PAS, 22 mmol of HBr, 12 mmol of 2-dimethylamino-pyridine, 9 mmol of bromine, 9.5 mmol of $NaNO_2$, 25 ml of acetonitrile and 2.5 ml of water were reacted to obtain a yield of 1.81 g of excellent quality. Monobromide, ethyl acetate ratio was 10.5:15. Maximum yield was 51.8% and estimated actual yield was 50% or more.

(g) with 4-dimethylamino-pyridine 8 mmol of amino-PAS, 22 mmol of HBr, 12 mmol of 4-dimethylamino-pyridine, only 9 mmol of bromine, 9.5 mmol of $NaNO_2$, 25 ml of acetonitrile and 2.5 ml of water were reacted to obtain a yield of 1.87 g of very good quality. Dibromide:monobromide:ethyl acetate ratio was 0.7:11.0:15.5. Maximum yield was 53.9% and estimated actual yield was at least 50%.

(h) with 2,6-dimethyl-pyridine 8 mmol of amino-PAS, 22 mol of HBr, 12 mmol of 2,6-dimethyl-pyridine, 12 mmol of bromine, 9.5 mmol of $NaNO_2$, 25 ml of acetonitrile, 2.5 ml of water were reacted to obtain a yield of 1.92 g of good quality. Dibromide:monobromide:ethyl acetate ratio was 11:4:1.7. Maximum yield was 63.1%. Estimated actual yield about 55%.

(i) with 3-methyl-isoquinoline 8 mmol of amino-PAS, 22 mmol of HBr, 12 mmol of 3-methyl-isoquinoline, only 9 mmol of bromine, 9.5 mmol of $NaNO_2$, 25 ml of acetonitrile and 2.5 ml of water were reacted to obtain a yield of 1.73 g of good to very good quality. Maximum yield was 63.9% and estimated actual yield was 55 to 57%. Dibromide:monobromide:ethyl acetate ratio was 2.3:9.8:1.6.

(j) with 4-methyl-pyridine-1-oxide 8 mmol of amino-PAS, only 10.5 mmol of HBr, 12 mmol of 4-methyl-pyridine-1-oxide, 12 mmol of bromine, 9.5 mmol of $NaNO_2$, 25 ml of acetonitrile and 1.3 ml of water were reacted to obtain a yield of 1.83 g of reasonably good quality. Dibromide:monobromide:ethyl acetate ratio was 8:5:1.2. Maximum yield was 62.1% and estimated actual yield was 50% or more.

(k) with triethylamine 8.0 mmol of amino-PAS, 22 mmol of HBr, 12 mmol of triethylamine, 12 mmol of bromine, 9.5 mmol of $NaNO_2$, 25 ml of acetonitrile and 2.5 ml of water were reacted to obtain a yield of 1.72 g of good to very good quality. Dibromide:monobromide:ethyl acetate:water ratio was 11.6:1.8:1.7. Maximum yield was 53.6% and estimated actual yield was about 48%.

(l) with 5,5-dimethyl-hydantoin

Exp (l)-1: 8 mmol of amino-PAS, 22 mmol of HBr, 12 mmol of 5,5-dimethyl-hydantoin, 12 mmol of bromine, 9.5 mmol of $NaNO_2$, 25 ml of acetonitrile and 2.5 ml of water were reacted to obtain a yield of 2.26 g of good quality. Dibromide:monobromide:ethyl acetate:dimethyl-hydantoin:water ratio was 3.1:2:1.8:1:4. Maximum yield was 67.4% and estimated actual yield was 58 to 60%. Exp(l)-2: 8 mmol of amino-PAS, only 11 mmol of HBr, 12 mmol of 5,5-dimethyl-hydantoin, 12 mmol of bromine, 9.5 mmol of $NaNO_2$, 25 ml of acetonitrile and 2.5 ml of water were reacted to obtain a yield of 2.30 g of reasonably good quality. Dibromide-monobromide:ethyl acetate:dimethylhydantoin:water ratio was 4:3:1.9:1.2:5. Maximum yield was 69.2% and estimated actual yield about was 60%.

(m) with 2-methyl-pyrazine 8 mmol of amino-PAS, 22 mmol of HBr, 12 mmol of 2-methylpyrazine, 12 mmol of bromine, 9.5 mmol of $NaNO_2$, 25 ml of acetonitrile and 2.5 ml of water were reacted to obtain a yield of 1.56 g of good quality. Monobromide:ethyl acetate:2-methylpyrazine:water ratio was 8.8:1.8:1.8:2. Maximum yield was 54.8% and estimated actual yield was about 50%.

A very similar experiment involving only 11 mmol of HBr produced in about the same yield and purity a product, as expected, consisting of a mixture of dibromide and the monobromide in a 2.3:4 molar ratio.

(n) with N-phenyl-phenylcarbonamide

Exp (n)-1: 8 mm-l of amino-PAS, 22 mmol of HBr, 12 mmol of N-phenyl-phenylcarbonamide, 12 mmol of bromine, 9.5 mmol of $NaNO_2$, 25 ml of acetonitrile and 2.5 ml of water were reacted to obtain a yield of 2.56 g of good to very good quality. Dibromide:monobromide:ethyl acetate:N-phenyl-phenylcarbonamide ratio was 10:1.5:1.4:4:3. Maximum yield was 68.8% and estimated actual yield was 62 to 64%.

Exp (n)-2: Identical with Exp (n)-1 except that only 11 mmol of HBr were used yielded 2.40 g of reasonably good quality. Dibromide:monobromide:ethyl acetate:N-phenylphenylcarbonamide ratio was 5:5.5:3.0:3.7. Maximum yield was 67.5% and estimated actual yield was about 60%.

(o) with N-ethyl piperidine 8 mmol of amino-PAS, 22 mmol of HBr, 12 mmol of N-ethyl-piperidine, 12 mmol of bromine, 9.5 mmol of $NaNO_2$, 25 ml of acetonitrile and 2.5 ml of water were reacted to obtain a yield of 1.61 g of very good quality. Dibromide:monobromide:ethyl acetate ratio was 12:2:1.8. Maximum yield was 51.5% and estimated actual yield was about 48%.

(p) with phthalimide

Exp (p)-1: 8 mmol of amino-PAS, only 11 mmol of HBr, 12 mmol of phthalimide, 12 mmol of bromine, 9.5 mmol of $NaNO_2$, 25 ml of acetonitrile and 2.5 ml of water were reacted to obtain a yield of 2.04 g of reasonably good quality. Dibromide:monobromide:ethyl acetate:phthalimide,water ratio was 7:3.5:1.7:0.5:3. Maximum yield was 65.0% and estimated actual yield was about 55%.

Exp (p)-2: Identical with Exp (p)-1 except that 22 mmol of HBr were used yielded 2.0 g of very good quality. Dibromide:monobromide:ethyl acetate:phthalimide ratio was 11.2:2.2:0.7:0.8. Maximum yield was 64.4% and estimated actual yield was 60%.

(q) with N-methyl-morpholine

Exp (q)-1: 8 mmol of amino-PAS, 22 mmol of HBr, 12 mmol of N-methyl-morpholine, 12 mmol of bromine, 9.5 mmol of $NaNO_2$, 25 ml of acetonitrile and 2.5 ml of water were reacted to obtain a yield of 2.0 g of good quality. Dibromide:monobromide:ethyl acetate ratio was 10:4:1.3. Maximum yield was 68.9% and estimated actual yield was 61 to 63%.

Exp (q)-2: Differed from Exp (q)-1 in the employment of 9 mmol of bromine and of 1,2-dimethoxyethane instead of acetonitrile to obtain a yield of 2.01 g of reasonably good quality. Dibromide monobromide:ethyl acetate:dimethoxyethane ratio was 5:6.4:2.3:0.25. Maximum yield was 68.6% and estimated actual yield was 58 to 60%.

(r) with hydantoin 8 mmol of amino-PAS, 22 mmol of HBr, 12 mmol of hydantoin, 12 mmol of bromine, 9.5 mmol of $NaNO_2$, 25 ml of acetonitrile and 2.5 ml of water were reacted to obtain a yield of 2.18 g of good to very good quality. Dibromide:monobromide:ethyl acetate:hydantoin ratio was 11.5:1:1.3:0.5. Maximum yield was 68.4% and estimated actual yield was 62 to 64%.

(s) with phenylacetyl urea 8 mmol of amino-PAS, 22 mmol of HBr, 12 mmol of phenylacetyl urea, 12 mmol of bromine, 9.5 mmol of $NaNO_2$, 25 ml of acetonitrile and 2.5 ml of water were reacted to obtain a yield of 2.07 g of good quality. Dibromide:monobromide:ethyl acetate:phenylacetyl urea:water ratio was 14.2:1.3:0.7:0.6:5. Maximum yield was 64.5% and estimated actual yield was 56 to 58%.

(t) with phenylacetamide

Exp (t)-1: 8 mmol of amino-PAS, 22 mmol of HBr, 12 mmol of phenylacetamide, 12 mmol of bromine, 9.5 mmol of $NaNO_2$, 25 ml of acetonitrile and 2.5 ml of water were reacted to obtain a yield of 2.25 g of good to very good quality. Dibromide:monobromide:ethyl acetate:phenylacetamide ratio was 10:1.2:1.2:1.0. Maximum yield was 69.3% and estimated actual yield was 62 to 64%.

Exp (t)-2: In this experiment, somewhat less of starting material and somewhat more of water were employed and no attempts were made for more or less quantitative removal of auxiliary agent. 7.35 mmol of amino-PAS, 22 mmol of HBr, 12 mmol of phenylacetamide, 12 mmol of bromine, 9.5 mmol of $NaNO_2$, 25 ml of acetonitrile and 2.7 ml of water were reacted to obtain a yield of 2.42 g of good to very good quality. Dibromide:monobromide:ethyl acetate:phenylacetamide:water ratio was 7.5:2:1:5.5:4. Maximum yield was 70.2% and estimated actual yield was 63 to 65%.

(u) with acetamide 8 mmol of amino-PAS, 22 mol of HBr, 12 mmol of acetamide, 12 mmol of bromine, 9.5 mmol of $NaNO_2$, 25 ml of acetonitrile and 2.5 ml of water were reacted to obtain a yield of 1.57 g of very good quality. Dibromide:monobromide:ethyl acetate:acetamide:water ratio was 9.5:3:1.5:0.4:9. Maximum yield was 49.4% and estimated actual yield was 45% or more.

(v) with N-phenyl-acetamide 7.35 mmol of amino-PAS, 22 mmol of HBr, 12 mmol of N-phenylacetamide, 12 mmol of bromine, 9.5 mmol of $NaNO_2$, 25 ml of acetonitrile and 2.7 ml of water were reacted to obtain a yield of 1.6 g of very good quality. Dibromide:monobromide:ethyl acetate:N-phenylacetamide:water ratio was 12:1.4:0.9:0.8:4. Maximum yield was 56.2% and estimated actual yield was 50 to 52%.

(w) with pyridyl-4-carbonamide 7.35 mmol of amino-PAS, 10.5 mmol of HBr, 10 mmol of p-tolylsulfonic acid, 12 mmol of pyridyl-4-carbonamide, 12 mmol of bromine, 9.5 mmol of $NaNO_2$, 25 ml of acetonitrile and 2.7 ml of water were reacted to obtain a yield of 2.00 g of reasonably good quality. Dibromide:monobromide:ethyl acetate:water ratio was 10:1.6:1:8. Maximum yield was 68.7% and estimated actual yield was 54 to 56%.

(x) with N-benzoyl-benzenesulfonamide 8 mmol of amino-PAS, 22 mmol HBr, 12 mmol of N-benzoyl-benzenesulfonamide, 12 mmol of bromine, 9.5 mmol of $NaNO_2$, 25 ml of acetonitrile and 2.5 ml of water were reacted to obtain a yield of 2.67 g of good to very good quality. Dibromide:monobromide:ethyl acetate:N-benzoyl-benzenesulfonamide ratio was 4.3:0.7:0.5:0.5 Maximum yield was 78.6% and estimated actual yield was 71 to 73%.

(y) with p-tolyl-sulfonamide 8 mmol of amino-PAS, 22 mol of HBr, 12 mmol of p-tolyl-sulfonamide, 12 mmol of bromide, 9.5 mmol of $NaNO_2$, 25 ml of acetonitrile and 2.5 ml of water were reacted to obtain a yield of 2.35 g of good and very good quality. Dibromide:monobromide:ethyl acetate:p-tolyl-sulfonamide:water ratio was 8:0.5:1:2:4. Maximum yield was 63.3% and estimated actual yield was 56 to 58%.

(z) with bis-(p-tolyl-sulfon)imide 8 mmol of amino-PAS, 22 ml of HBr, 12 mmol of bis(p-tolyl-sulfon)imide, 12 mmol of bromine, 9.5 mmol of $NaNO_2$, 25 ml of acetonitrile and 2.5 ml of water were reacted to obtain a yield of 2.16 of good quality. Dibromide:monobromide:ethyl acetate:bis(p-tolyl-sulfon)imide ratio was 8.0:2.0:0.8:0.5. Maximum yield was 67.7% and estimated actual yield was about 60%.

EXAMPLE 9

Examples of the influence of the nature of the auxiliary agent on the yield of useful products in the diazotization-bromination of 6-β-amino-penicillanic-acid-1,1-dioxide (see Example 8)

(a) reaction in the presence of saccharin 8 mmol of amino-PAS, 22 mmol of HBr, 12 mmol of saccharin, 12 mmol of bromine, 9.5 mmol of $NaNO_2$, 25 ml of actonitrile and 2.5 ml of water were reacted to obtain a yield of 2.12 g of good quality. Dibromide:monobromide:ethyl acetate:saccharin ratio was 8.0:2.0:1.0:1.0. Maximum yield was 64.8% and estimated actual yield was 55 to 57%.

(b) with 1-methyl-imidazole 7.7 mmol of amino-PAS, 22 mmol of HBr, 12 mmol of 1-methyl-imidazole, 12 mmol of bromine, 9.5 mmol of $NaNO_2$, 25 ml of nitromethane and 2.6 ml of water were reacted to obtain a yield of 1.84 g of good to very good quality. Dibromide:monobromide:ethyl acetate ratio was 11:1.4:1.7. Maximum yield was 60.6% and estimated actual yield was 54 to 56%.

(c) with succinimide

Exp(c)-1: 8 mmol of amino-PAS, 22 mmol of HBr, 12 mmol of succinimide, only 9 mmol of bromine, 9.5 mmol of $NaNO_2$, 25 ml of acetonitrile and 2.5 ml of water were reacted to obtain a yield of 2.21 g of good to very good quality. Dibromide: monobromide:ethyl acetate ratio was 3:13.5:23. Maximum yield was 61.5% and estimated actual yield was 55 to 57%.

Exp(c)-2: Identical with Exp(c)-1 except that 12 mmol of bromine were used to obtain a yield of 2.32 g of good quality as the product contained only one visible degradation product (about 5 to 6 mmol %) Dibromide:monobromide:ethyl acetate ratio was 3:6.5:3.6. Maximum yield was 78.3% and estimated actual yield was 70 to 72%.

Exp(c)-3: Identical with Exp(c)-2 except that 7.35 mmol of amino-PAS and 2.7 ml of water were used to obtain a yield of 2.21 g of very good quality. Dibromide:monobromide:ethyl acetate:succinimide ratio was 14:1:3:2. Maximum yield was 72.1% and estimated actual yield was 67 to 69%.

Exp(c)-4: 7.7 mmol of amino-PAS, 22 mmol of HBr, 12 mmol of succinimide, 12 mmol of bromine, 9.5 mmol of $NaNO_2$, 22.5 ml of ethyl acetate, 2.5 ml of sulfolane and 2.6 ml of water were reacted to obtain a yield of 1.93 g of very good quality. Dibromide:ethyl acetate:sulfolane:succinimide ratio was 10.5:1.4:1.7:2.0. Maximum yield was 57.1% and estimated actual yield was 52 to 53%.

Exp(c)-5: 7.35 mmol of amino-PAS, no HBr, 22 mmol of p-tolyl-sulfonic acid, 12 mmol of bromine, 9.5 mmol of $NaNO_2$, 30 ml of acetonitrile and 2.7 ml of water were reacted to obtain a yield of only 1.38 g: insofar as useful product was present it consisted mainly of the monobromide. Calculation of yield was not feasible because of too poor a quality.

Exp(c)-6: Same as Exp(c)-2 but the amounts of succinimide and bromine were raised to 15 mmol and the amount of $NaNO_2$ to 12 mmol to obtain a yield of 2.48 g of good to very good quality. Dibromide:monobromide:ethyl acetate:succinimide ratio was 16:0.5:1.1:3. Maximum yield was 73.0% and estimated actual yield was 66 to 68%.

Exp(c)-7: Same as Exp(c)-6 but the amount of succinimide was 12 mmol to obtain a yield of 2.2 g of good to very good quality. Dibromide:monobromide:ethyl acetate:succinimide:water ratio was 12.2:0.7:0.7:3.5:6. Maximum yield was 66.7% and estimated actual yield was 60 to 62%.

Exp(c)-8: 8 mmol of amino-PAS, 22 mmol of HBr, 12 mmol of N-bromo-succinimide, 9.5 mmol of $NaNO_2$, 25 ml of acetonitrile and 2.5 ml of water were reacted to obtain a yield of 2.09 g of reasonably good quality. Dibromide-monobromide:ethyl acetate ratio was 10.5:4.1:1.5. Maximum yield was 69.1% and estimated actual yield was 59 to 62%.

NOTE—It seems reasonable to assume that in the presence of excess hydrobromic acid, N-bromo-succinimide will be decomposed rapidly into mainly bromine and succinimide. If so, the mixture will contain already before introduction of $NaNO_2$ is started, an approximately 10:12:12 ratio of HBr, succinimide and bromine and the excess of dibromide over monobromide in the isolated product supports such as assumption. The substantially lower yield of useful products as compared with Exp(c)-2 caused by a too low amount of HBr is then also logical.

(d) with 1-vinyl-imidazole 8 mmol of amino-PAS, 22 mmol of HBr, 12 mmol of 1-vinyl-imidazole, 12 mmol of bromine, 9.5 mmol of $NaNO_2$, 25 ml of acetonitrile and 2.5 ml of water were reacted to obtain a yield of 2.44 g of at least good quality. Dibromide:monobromide:ethyl acetate ratio was 16.2:1.6:1.5. Maximum yield was 77.8% and estimated actual yield was at least 70%.

(e) with diphenyl sulfoxide 8 mmol of amino-PAS, 22 mmol of HBr, 12 mmol of diphenyl sulfoxide, 12 mmol of bromine, 9.5 mmol of $NaNO_2$, 25 ml of acetonitrile and 2.5 ml of water were reacted to obtain a yield of 2.00 g of good to very good quality. Dibromide:monobromide:ethyl acetate:water ratio was 15.2:1.1:1.8:3. Maximum yield was 65.2% and estimated actual yield was 59 to 62%.

(f) with caprolactam 8 mmol of amino PAS, 22 mmol of HBr, 12 mmol of caprolactam, 12 mmol of bromine, 9.5 mmol of $NaNO_2$, 25 ml of acetonitrile and 2.5 ml of water were reacted to obtain a yield of 2.40 g of at least good quality. Dibromide:monobromide:ethyl acetate ratio was 11.7:1.6:1.6. Maximum yield was 78.0% and estimated yield was 69 to 72%.

(g) with 1,1,3,3-tetramethylquanidine 8 mmol of amino-PAS, 22 mmol of HBr, 12 mmol of 1,1,3,3-tetramethylguanidine, 12 mmol of bromine, 9.5 mmol of $NaNO_2$, 25 mmol of acetonitrile and 2.5 ml of water were reacted to obtain a yield of 2.24 g of good quality. Dibromide:monobromide:ethyl acetate:water ratio was 10.2:1.6:1.5:3. Maximum yield was 70.7% and estimated actual yield was 62 to 64%.

(h) with pyridine in an inverted procedure 8 mmol of amino-PAS were added portion-wise at 0°–5° C. over 30 minutes to a mixture consisting of 22 mmol of HBr, 12 mmol of pyridine, 12 mmol of bromine, 9.5 mmol of $NaNO_2$, 25 ml of acetonitrile and 2.5 ml of water followed by 15 minutes additional stirring to obtain a yield of 2.21 g of reasonably good quality. Dibromide:monobromide:ethyl acetate ratio was 13.5:2.2:2.3. Maximum yield was 70.3% and estimated actual yield was 58 to 61%.

(i) with dimethylsulfone 8 mmol of amino-PAS, 22 mmol of HBr, 12 mmol of dimethylsulfone, 12 mmol of bromine, 9.5 mmol of $NaNO_2$, 25 ml of acetonitrile and 2.5 ml of water were reacted to obtain a yield of 2.50 g of at least good quality. Dibromide:monobromide:ethyl acetate:dimethylsulfone ratio was 14.5:1.1:1.4:2.5. Maximum yield was 76.5% and estimated actual yield was 68 to 70%.

(j) with pyrrolidine-2-one 8 mmol of amino-PAS, 22 mmol of HBr, 12 mmol of pyrrolidin-2-one, 12 mmol of bromine, 9.5 mmol of $NaNO_2$, 25 ml of acetonitrile and 2.5 ml of water were reacted to obtain a yield of 2.06 g of at least good quality. Dibromide:monobromide:ethyl acetate:pyrrolidin-2-one:water ratio was 8:4.6:2:1.4:2. Maximum yield was 66.3% and estimated actual yield was 59 to 61%.

(k) with guanidine 8 mmol of amino-PAS, 22 mmol of HBr, 12 mmol of the hydrogen chloride of guanidine, 12 mmol of bromine, 9.5 mmol of $NaNO_2$, 25 ml of acetonitrile and 2.5 ml of water were reacted to obtain a yield of 2.08 g of at least good quality. Dibromide:monobromide:ethyl actate:water ratio was 10.2:3.5:1.8:6. Maximum yield was 66.6% and estimated actual yield was 60 to 62%.

(l) with dicyanomethane 8 mmol of amino-PAS, 22 mmol of HBr, 12 mmol of dicyanomethane, 12 mol of bromine, 9.5 mmol of $NaNO_2$, 25 mol of acetanitrile and 2.5 ml of water were reacted to obtain a yield of 2.32 g of good quality. Dibromide:monobromide:ethyl acetate:dicyanomethane ratio was 9:4.5:2.4:6. Maximum yield was 70.8% and estimated actual yield was 62 to 65%.

(m) with 1,2-dicyano-ethane 8 mmol of amino-PAS, 22 mmol of HBr, 12 mmol of 1,2-dicyano-ethane, 12 mmol of bromine, 9.5 mmol of $NaNO_2$, 25 ml of ethyl acetate and 2.5 ml of water were reacted to obtain a yield of 2.45 g of very good quality. Dibromide:monobromide:ethyl acetate:1,2-dicyanoethane ratio was 12.6:1.2:1.6:9.7. Maximum yield was 68.0% and estimated actual yield was 61 to 64%.

EXAMPLE 10

Diazotization-bromination on a larger scale of 6-β-amino-penicillanic acid-1,1-dioxide into 6,6-dibromo-penicillanic acid-1,1-dioxide and 6-α-bromo-penicillanic acid-1,1-dioxide in the presence of 1-methyl-imidazole (a) Repetition of Example 8(c) on 40 mmol scale.

With stirring and at a temperature of below 5° C., 10 g (40 mmol) of 6-β-amino-penicillanic acid-1,1-dioxide were added to a solution of 12.5 ml of 47% hydrogen bromide in water (equivalent to 110 mmol of HBr) in 125 ml of acetonitrile prepared in the cold and the starting material dissolved almost instantaneously. Immediately thereafter were added sequentially 4.95 ml (60 mmol) of 1-methyl-imidazole and 2.30 ml (45 mmol) of bromine and as soon as the resulting mixture by means of external cooling with a mixture of water and crushed ice regained a temperature of below 5° C., 3.3 g (47.5 mmol) of sodium nitrite were added in about five equal portions over a period of approximately 10 minutes followed by additional stirring during 30 minutes. Still keeping the temperature at or below 5° C., a solution of 5 g of sodium metabisulfite ($Na_2S_2O_5$) in 100 ml of water were added cautiously immediately followed by addition of 4N sodium hydroxide until a pH of approximately 5 was reached. The resulting solution was over a period of 10–15 minutes submitted to concentration in vacuo at 12–20 mm Hg to remove acetonitrile azeotropically. The pH of the resulting solution was raised with 4N sodium hydroxide to 6.0 to 6.5 followed by two extractions with about 200 ml volumes of dichloromethane. By adding 4N hydrochloric acid, the pH of the resulting, somewhat purified, solution was brought to 2.0, followed by three extractions with 100 to 150 ml volumes of ethyl acetate at a pH of approximately 2.0. To the combined extract was added 5 ml of a saturated solution of sodium chloride in water, followed by thorough shaking of the mixture and separation of layers. This purification of the combined extract was repeated with about 10 ml of the saturated sodium chloride solution. The extract was dried over anhydrous magnesium sulfate, filtered, the filter cake was washed three times with a small volume of ethyl acetate, and the combined filtrates were in vacuo evaporated. The resulting product was dried in vacuo to obtain a yield of 9.83 g.

With respect to the presence of unknown degradation products, the isolated product was of reasonably good quality according to TLC and the PMR spectrum taken at 60 Mc from a solution in $d_6$-DMSO with tetramethyl-silane as internal reference. The spectrum showed a 8:28:18 molar ratio between 6,6-dibromo-penicillanic acid-1,1-dioxide, 6-α-bromo-penicillanic acid-1,1-dioxide and ethyl acetate and the calculated maximum yield was 65.8%. Since the quality was estimated to be slightly less than good, the actual yield was probably somewhat less than 65.8% minus 10% of 65.8%, which is 59.3%. A spectrum taken from weighed amounts of a reference and of the products indicated an actual yield of 55.4% of useful products.

(b) Repetition of Example 8(b) on a 40 mmol scale

By introducing 3.10 ml (or 60 mmol) of bromine, Exp (a) was repeated in identical fashion to obtain a yield of 9.98 g of good to very good quality, Dibromide;monobromide:ethyl acetate ratio was 9:6:1.5. Calculated maximum yield was 67.8% and as the quality of this product is substantially better than the quality of the product prepared under (a), the estimated actual yield will be probably 67.8% minus 5–10% of 67.8%, which means an actual yield of 61 to 64%.

Comparison of the results of this Example with the corresponding results of Example 8(b) and (c) indicate that at least with some tertiary amines employed as auxiliary agents, scale enlargement appears to be possible even without optimalization or deliberate adaption to larger scale and that the arbitrary indication of estimated actual yields is on the whole related to the fact that even without the safety precaution the yields are not corrected for the presence of water in the starting material or for its purity.

EXAMPLE 11

Diazotization-bromination in the presence of 5,5-dimethylhydantoin

The experiments described hereinafter were performed to assess the possibility of scale enlargement in the case of use of an amide bond containing auxiliary agent and 5,5-dimethyl-hydantoin was chosen for this purpose as it produces in the diazotizaton-bromination yields of intermediate magnitude under standard conditions used throughout in the preparations of Examples 8 and 9. The scale of Example 8(l)-1 was therefore increased six times, but for the rest of Example 11 is an exact copy of Example 8(l)-1 but for one alteration in that no serious attempts were made to remove the auxiliary agent, either by more exhaustive purification of the aqueous layer after diazotization by extraction with dichloromethane at pH 6–6.5 or by purification of the aqueous layer after the reduction by extraction with, for example, ethyl acetate at about pH 5, which is a more expedient way of removal of this auxiliary agent. The reduction step itself served as an example for the feasibility of reduction in a two phase system, thereby omitting actual isolation and re-dissolution of the mixture of bromides.

With cooling using iced water, 12 g (48 mmol) of 6-β-amino-penicillanic acid-1,1-dioxide were dissolved with stirring in a solution of 15 ml (132 mmol) of 47% hydrobromic acid in 150 ml of acetonitrile and while continuously operating at 0°–5° C., there were added sequentially 9.24 g (72 mmol) of 5,5-dimethyl-hydantoin and 3.72 ml (72 mmol) of bromine immediately followed by the introduction of 3.96 g (57 mmol) of sodium nitrite in about five equal portions over a period of 10–15 minutes. After 30 minutes of additional stirring, a solution of 6 g of sodium metabisulfite in 60 ml of water and 4N sodium hydroxide were introduced cautiously with stirring. After the pH had reached about 6.5, acetonitrile was removed by concentration in vacuo followed by two extractions with 60 ml volumes of dichloromethane. The remaining solution in water was extracted at pH 2.0 three times with 150 ml volumes of ethyl acetate. The combined extract was twice washed with a small volume of saturated sodium chloride solution and subsequently mixed with 150 ml of cold water whereupon the pH was brought to 3.5 by addition of 4N sodium hydroxide.

EXAMPLE 12

Diazotization-bromination of 6-β-amino-penicillanic acid-1,1-dioxide to mixtures of 6,6-dibromo-penicillanic acid-1,1-dioxide and 6-α-bromo-penicillanic acid-1,1-dioxide with an alkyl nitrite as nitrosating agent In the preceding Examples diazotization-bromination of 6-β-amino-penicillanic acid-1,1-dioxide, in all probability involving the very water sensitive intermediate 6-diazonium-penicillanate-1,1-dioxide, or its conjugate acid, was always carried out with an alkali metal nitrite as nitrosating agent. The Examples given indicate that the same type of reaction can also be carried out with an alkyl or cycloalkyl nitrite as nitrosating agent. The results furthermore indicate that good yields may likewise result eventually, but that an optimized procedure probably will involve a somewhat different multiple molar ratio between starting material, acid, hydrobromic acid, bromine, auxiliary agent and water as compared with a similar optimized procedure involving the same auxiliary agent, but with sodium nitrite as nitrosating agent. Although various (cyclo)alkyl nitrites can be used, in the Examples given hereinafter there was employed throughout pentyl nitrite, a cheap agent of commercial origin consisting of an almost exact 3:1 mixture of pentyl-2-nitrite and pentyl-1-nitrite.

The method empoloyed in small (about 8 mmol) scale experiments was very similar to the method used for conversions with sodium nitrite indicated in the preceding Examples except pentyl nitrite was added in one portion followed by 45 minutes stirring at 0°–5° C. The isolation procedure was also as described before and always involved washing of the solution in water with dichloromethane at pH 6.0 to 6.5 before extraction of product with ethyl acetate at pH 2. The experiments therefore are treated in the abbreviated form as employed in the Examples 8 and 9.

(a) reaction in the presence of 1-methylimidazole 8 mmol of 6-amino-PAS, 22 mmol of HBr, 12 mmol of 1-methyl-imidazole, 12 mmol of bromine, 12 mmol of pentyl nitrite, 25 ml of acetonitrile and 2.5 ml of water were reacted to obtain a yield of 2.19 g of reasonably good quality. Dibromide:monobromide:ethyl acetate ratio was 13:2:0.7. Maximum yield was 71.2% and estimated actual yield was 61 to 63%.

(b) with 1-methyl-imidazole 8 mmol of 6-amino-PAS, 22 mmol of HBr, 12 mmol of 1-methyl-imidazole, 12 mmol of bromine, 11 mmol of pentyl nitrite, 30 ml of acetonitrile and 2.5 ml of water were reacted to obtain a yield of 2.09 g of good quality. Dibromide:monobromide:ethyl acetate ratio was 12:2:0.8. Maximum yield was 67.9% and estimated actual yield was 60 to 62%.

(c) with pyridine 8 mmol of amino-PAS, 28 mmol of HBr, 12 mmol of pyridine, 12 mmol of bromine, 16 mmol of pentyl nitrite, 25 ml of acetonitrile and 3.2 ml of water were reacted to obtain a yield of 2.65 g of only reasonable quality. Dibromide:monobromide:ethyl acetate ratio was 9.5:3:1. Maximum yield was 87.4% and estimated actual yield was around 70%, perhaps more.

(d) with pyridine 8 mmol of amino-PAS, 10.5 mmol of p-tolyl-sulfonic acid, 8.0 g (25 mmol) of pyridine hydrobromide perbromide, 16 mmol of pentyl nitrite, 25 ml of acetonitrile and no extra water were reacted to obtain a yield of 1.92 g of only reasonable quality. Dibromide:monobromide:ethyl acetate:water ratio was 13:1:0.9:5. Maximum yield was 60.4% and estimated actual yield was about 50%.

EXAMPLE 13

Diazotization-bromination in the presence of excess acid with pentyl nitrite (a) Continuously operating at 0°–5° C., 12 g (48 mmol) of 6-$\beta$-amino-penicillanic acid-1,1-dioxide were dissolved in a mixture of 19.2 ml of a 47% aqueous solution of hydrogen bromide (168 mmol) in water and 150 ml of acetonitrile followed by the introduction of 5.7 ml (72 mmol) of pyridine and 3.72 ml (72 mmol) of bromine. A solution of 12 ml (96 mmol) of pentyl nitrite in 30 ml of acetonitrile was added dropwise over 10–15 minutes followed by 30 minutes additional stirring. The resulting reaction mixture was treated in usual fashion: addition of dilute sodium metasulfite and of 4N sodium hydroxide to pH 6.0 to 6.5, removal of acetonitrile in vacuo, two extractions with dichloromethane, extraction of the desired products with ethyl acetate at pH 2.0 and washing of the combined ethyl acetate layers with a small volume of sodium chloride solution.

(b) Experiment (a) was repeated with another auxiliary agent, while using somewhat more appropriate conditions. Continuously operating at 0°–5° C., 12 g (48 mmol) of the starting material were dissolved in a mixture of 9.18 g (48 mmol) of the monohydrate of p-tolyl-sulfonic acid, 15 ml of a 47% aqueous solution of hydrogen bromide, (130 mmol of HBr) and 150 ml of acetonitrile followed by the introduction of 6.0 ml (72 mmol) of 1-methyl-imidazole and 3.72 ml (72 mmol) of bromine. 10.5 ml (84 mmol) of pentyl nitrite were added dropwise in 10–15 minutes followed by 30 minutes additional stirring. The resulting reaction mixture was treated in the usual fashion as indicated under (a). After washing with a small volume of a saturated sodium chloride, the final solution in ethyl acetate was dried over anhydrous magnesium sulfate and filtered. The filtrate was evaporated in vacuo to obtain a yield of 6.22 g. The PMR spectrum indicated very good quality and a molar ratio between 6,6-dibromo-penicillanic acid-1,1-dioxide, 6-$\alpha$-bromo-penicillanic acid-1,1-dioxide, ethyl acetate and pentanols of 10.6:3.6:1:2. The calculated maximum yield was 66.5% and the estimated actual yield was 60 to 63%.

EXAMPLE 14

Preparation of potassium 6-$\alpha$-bromo-penicillanate 1,1-dioxide

While continuously maintaining an internal temperature of 0°–5° C., 20 g (80 mmol) of 6-$\beta$-amino-penicillanic acid-1,1-dioxide were dissolved with rapid stirring in a mixture of 300 ml of acetonitrile and 28.5 ml of a 47% solution of hydrogen bromide in water (equivalent to about 250 mmol of HBr) immediately followed by introduction of 15 ml (about 120 mmol) of 2-dimethylamino-pyridine and 6.2 ml (120 mmol) of bromine. 6.6 g (95 mmol) of sodium nitrite were added in six equal portions over 15–20 minutes followed by additional stirring for 30–40 minutes. By careful addition of 4N sodium hydroxide, the pH of the well stirred mixture was slowly raised to 6.5 while at the same time a solution of 10 g of sodium metabisulfite in 100 ml of cold water was added regularly at pH 2 to 4. Acetonitrile was removed in vacuo and then the volume of the solution in water was increased to about 200 ml. The solution was twice extracted at pH 6.5 with 150 ml volumes of dichloromethane and the combined organic phase was washed once with 50 ml of water and then discarded. 200 ml of ethyl acetate were added with stirring to the combined aqueous layers whereupon the pH was brought to 2.0 by addition of 4N hydrochloric acid. After separation of layers, the aqueous layer was extracted three more times at pH 2 with 150 ml volumes of ethyl acetate and 5 ml of a saturated solution of sodium chloride in water was shaken with the combined ethyl acetate extract. After separation of layers, washing was repeated using 10 ml of saturated sodium chloride. Activated carbon was added with stirring to the solution in ethyl acetate followed after 30 minutes by introduction of anhydrous magnesium sulfate. The preparation was filtered through a filter aid including washing with ethyl acetate and the filtrate was evaporated in vacuo to a slightly colored solid. After drying in vacuo, the yield was 20.7 g and the PMR spectrum indicated a 2:3 molar ratio between 6-$\alpha$-amino-penicillanic acid-1,1-dioxide and ethyl acetate. The quality of the product was good and contamination by the 6,6-dibromide was negligeable. The maximum yield was calculated to be 58% and the actual yield was estimated to be 51 to 53%.

20 g of this product were dissolved in a minimal volume of ethyl acetate whereupon potassium $\alpha$-ethyl-capronate (an about 5N solution in butanol) was added in slight excess and seeding resulted in a crystalline product. After slow addition of an about equal volume of diethyl ether with shaking, the product was collected by filtration, washed with cold ethyl acetate and with diethyl ether and after drying in vacuo, the yield of the potassium salt of 6-$\alpha$-bromo-penicillanic acid-1,1-dioxide was 13 g.

EXAMPLE 15

Preparation of solutions of crude 6-diazo-pencillanic acid-1,1-dioxide 2.0 g of 6-β-amino-penicillanic acid-1,1-dioxide (containing 6 to 7% by weight of water) were suspended under a nitrogen atmosphere with stirring in 25 ml of good grade acetonitrile and at about 20° C. and with stirring, 1.5 ml (about 50% excess) of n-pentyl-nitrite (Merck-Schuchardt in actual fact a 3:1 mixture of pentyl-2-nitrite and pentyl-1-nitrite) were added in one portion. Conversion was indicated by an about 3° C. rise in temperature and by gradual dissolution of the sparingly soluble starting material and there was practically no development of nitrogen discernible. After 15 minutes of additional stirring, a tiny part of the reaction mixture was submitted to thin-layer chromatography on silica with 98:2 ethyl acetate/formic acid as the eluant. Upon inspection with UV light and iodine azide/starch spray, the plate showed a large spot at Rf about 0.5 and very much smaller spots at the start and at Rf about 0.4, the latter probably indicating contamination by a very small amount of an undesired side-product, viz. 3,3-dimethyl-8-oxo-1-aza-4-thia-7-oxa-bicyclo[3,3,0]octane-2-carboxylic acid 4,4-dioxide. A small volume of the reaction mixture diluted with acetonitrile was submitted to IR spectroscopy with acetonitrile as the blank and the spectrum obtained showed an absorption of substantial intensity at 2150 cm$^{-1}$ attributable to the diazo group.

(1) TLC and IR therefore may indicate a very good, possibly about 90%, conversion of the starting material into 6-diazo-penicillanic acid-1,1-dioxide in spite of the presence of water in the starting material and in the solvent which was not dried.

(2) Suspension of the starting material in a number of other good grade, but not deliberately dried non-hydroxyl solvents such as tetrahydrofuran and other ether type solvents, methyl acetate and ethyl acetate were also suited for conversion at room temperature with alkyl nitrites to solutions of 6-diazo-penicillanic acid-1,1-dioxide of about the same apparent quality. For reasons of too small solubility or of subsequent reactions of the diazo group with solvent, unsuitable solvents were halogenated hydrocarbon solvents such as dichloromethane (too low solubility), some hydroxyl solvents like ethanol and solvents containing a reactive carbonyl group such as acetone in which, in contrast with experiments involving ethanol, substantial dissolution of starting material did occur but was accompanied by substantial degradation or conversion of the 6-diazo-penicillanic acid-1,1-dioxide.

(3) The bicyclo[3,3,0]octane-2-carboxylic acid 4,4-dioxide mentioned above may be present as a slight impurity because of the Rf-value which is identical with the Rf of the authentic compound and since it was experienced several times, that nitrosation of the starting material under variable conditions of intermediate acidity—i.e. between about pH 2 and pH 5—optionally in the presence of bromide anions, but especially in the absence of bromine, this product participates in the reaction products mixture, very probably if not certainly as a consequence of a reaction of water with a nitrosated intermediate, but not with the diazo group or the diazonium group. The result of the underlying reaction mechanism is insertion of the oxygen atom of the water molecule between the original carbon six and carbon seven atoms of the bicyclo moiety. The best way found to prepare this bicyclic compound is addition of sodium nitrite to a solution of 6-β-amino-penicillanic acid-1,1-dioxide in water made by dissolution of the triethylamine salt of the starting material at pH 4.5 to 5.0. Under these conditions, conversion of starting material to the bicyclo compound amounts to about 80% or more and while extraction with ethyl acetate is simple, the compound can be obtained easily and in pure form in this manner. The identity of the compound 3,3-dimethyl-8-oxo-1-aza-4-thia-7-oxa-bicyclo[3,3,0]octane-2-carboxylic acid 4,4-dioxide was ascertained by a mass spectrogram of the derived methyl ester obtained by reaction with diazomethane establishing the molecular weight 249 of the ester, and by the IR and PMR spectra of this stable, hitherto unknown bicyclic sulfone carboxylic acid (after conversion to the potassium salt)

IR (KBr-disc, values in cm$^{-1}$): 3250,3200, 1758 (very intensive), 1615 (very intensive), 1452, 1395 (intensive), 1342 (intensive), 1308 (intensive), 1260, 1200 (very intensive with shoulders), 1180 (sh), 1140, 1105 (intensive), 1080, 1035, 988, etc.

PMR (d$_6$DMSO and a few droplets of DCO$_2$D, TMS, 60 Mc, δ-values in ppm): 1.43 (s, 3H), 1.52 (s, 3H), 4.45 (s, 1H), 4.62–5.34 (ABC splitting pattern with the C$_5$—H multiplet at about 5.25, 3H).

(4) In spite of the presence of small but about equimolar amounts of hydroxyl compounds, i.e. water and pentanol, such about 90% pure solutions of 6-diazo-penicillanic acid-1,1-dioxide are surprisingly stable at or below 0° C. and therefore can be stored. Since complete destruction during storage at room temperature which takes several days for completion as well as at 50° C., which takes several hours did result in a mixture of products in which another new compound dominates, decomposition at 50° C. was also carried out in the presence of an about 12 mol % excess of ethyl tetrolate (1-methyl-2-carbethoxy-ethyne). Decomposition was now complete in about 30 minutes and the new, in itself also unstable, compound participated in the reaction product to an appreciably larger extent. The compound was isolated in about 40% yield as a not completely pure product by collection of precipitates after repeated concentrations in vacuo combined with cooling and dilution with diethyl ether as well as lyophilization. 1.19 g of partly crystalline material were obtained starting from 2.0 g. of 6-β-amino-penicillanic acid-1,1-dioxide.

Acceleration of decomposition was carried out as the new compound was first supposed to be 5,5-dimethyl-4,5-dihydro-thiazole-3-carboxylic acid-1,1-dioxide generated by thermal fragmentation into this compound and hypothetical diazoketene which could then be trapped by ethyl tetrolate. This structure however had to be rejected on various grounds. The new compound does arise from interaction of water with the 6-diazo-derivative with expulsion of nitrogen which is facilitated by the presence of ethyl tetrolate. The IR spectrum of the product (KBr-disc, values of cm$^{-1}$) was rather unsharp as a consequence of the outspoken hydroscopic nature of the compound. The main absorptions were 1720–1760 (carboxylic group(s)), about 1640 (C=C?), 1570, 1390–1480, about 1290, about 1240 and 1070 and the spectrum indicated the presence of a considerable amount of water. The fairly nice quality with respect to other sulfur-containing compounds indicated by TLC was confirmed by the PMR-spectrum (d$_6$-DMSO, δ-values in ppm, TMS, 60 Mc), neglecting the presence of about ⅓ mole of acetic acid and about 2 moles of water per mole of compound: $C(CH_3)_2$: 1.04 (s, 3H) and 1.33 (s, 3H); $C_5$—H: 5.69 (s, 1H) and $C_2$—H: 8.82 (s, 1H). The spectrum indicated the presence of 4–6 mol % of another compound also having two $CH_3$—singlet signals and two C—H singlet signals which probably arises from rearrangement of the main product.

As indicated by the attribution of absorption signals of the PMR-spectrum, the new compound is believed to be 6,6-dimethyl-5,6-dihydro-(4H)thiazine-3,5-dicarboxylic acid-1,1-dioxide, for which a mechanism of formation can be indicated. Further structure identification, for instance presumably possible via transformation into the mono ester or diester by reaction with diazomethane, was not undertaken as this compound as well as 3,3-dimethyl-8-oxo-1-aza-4-thia-7-oxa-bicyclo[3,3,0]octane-2-carboxylic acid 4,4-dioxide does not have antibiotic properties. These two new compounds were described here for further identification of 6-diazo-pencillanic acid-1,1-dioxide which is an essential feature of the invention and by way of illustration of the difficulties, which had to be mastered, to arrive at suitable diazotization procedures for 6-β-amino-penicillanic acid-1,1-dioxide of the invention.

EXAMPLE 16

Preparation of crude potassium 6-diazo-penicillanate 1,1-dioxide 2.0 g of 6-β-amino-penicillanic acid-1,1-dioxide were suspended with stirring in 25 ml of methyl acetate and the reaction with phenyl nitrite was carried out as described in Example 14. After completion of the conversion monitored with TLC, an about 1 molar solution of potassium α-ethyl-capronate in n-butanol was added gradually at about 10° C. until the mixture attained a pH of 6.5. As precipitation did not occur, 50 ml of anhydrous diethyl ether were added dropwise with stirring and after standing for 30 minutes at 0°–5° C., the precipitate was collected by filtration, quickly washed with cold methyl acetate and thereafter with diethyl ether. The hydroscopic, yellowish solid was dried in vacuo in the presence of a desiccant over several hours to obtain a yield of 2.2 g of the potassium salt of 6-diazo-penicillanic acid-1,1-dioxide which appeared to be reasonably stable upon storage in the refrigerator. It was analyzed and investigated by means of TLC, IR and PMR.

TLC: A tiny amount was dissolved in ice-cold water and the solution was directly submitted to TLC on silica with 98:2 ethyl acetate/formic acid. Detection with UV light after drying of the plate and with iodine azide/-starch after heating to 150° C. showed a non-negligeably sized spot at the start (one or more degradation products) and one large spot at Rf of about 0.5 (the desired product). The solution was left standing at about 18° C. for about 1 hour. TLC on silica in 80:20:1 acetonitrile:water:formic acid showed massive but still not complete degradation into a thiazine 1,1-dioxide compound (Rf 0.24, visible under UV light, almost non-detectable with iodine azide/starch). This conversion of 6-diazo-penicillanic acid-1,1-dioxide (Rf is 0.72 in this system) went in an almost selective fashion. Notably, formation of 3,3-dimethyl-8-oxo-1-aza-4-thia-7-oxa-bicyclo[3,3,0]octane-2-carboxylic acid-4,4-dioxide was not discernible on the plate.

IR: (KBr-disc, values in $cm^{-1}$): very intensive absorption at 1780 (β-lactam) and 1630 (carboxylate anion), intensive absorptions at 2155 (diazo group) and 1335 ($SO_2$), slightly less intensive absorptions at 1400, 1265, 1170 and 1135 and minor absorptions at about 3000, 1485, 1060, 820 and several others between 1040 and 640. The spectrum also indicated the presence of water.

PMR ($d_6$-DMSO, δ-values in ppm, TMS, 60 Mc): The spectrum indicated presence of about 1 mole of water per mole of compound and minor contamination by acetic acid, methyl acetate, diethyl ether and α-ethyl-caproate due to the non-crystalline nature of the product, but degradation products were virtually absent. 6-Diazo-penicillanic acid-1,1-dioxide exhibited the following absorptions: $C(CH_3)_2$: 1.36 (s, 3H), 1.46 (s, 3H); $C_3$—H: 3.66 (s, 1H) and $C_5$—H: 5.81 (s, 1H).

Addition of a small amount of $DCO_2D$ resulted in extensive degradation of mainly the thiazine 1,1-dioxide compound and when taken at 25° C., a solution of the product in $D_2O$ gave a spectrum exhibiting immediate and progressive degradation into the same substance in an almost clean conversion as was also noted during TLC.

(a) Careful comparison of the integrals of absorptions belonging to water and the various impurities cited above with the absorption integrals of the diazo-derivative resulted in a calculated yield of 1.67 g instead of 2.22 g or an isolation yield of slightly over 70%. This result practically proved the very good conversion of 6-β-penicillanic acid-1,1-dioxide into 6-diazo-penicillanic acid-1,1-dioxide as indicated by TLC in Example 14.

(b) The corresponding crude sodium salt was prepared likewise and in approximately the same yield from an in situ prepared solution in ethyl acetate. Drier conditions during the preparation of the 6-diazo-derivative and its salts did not result in substantially greater yields. In the absence of different acids, 6-diazo-penicillanic acid-1,1-dioxide and its salts are apparently moderately stable in the presence of a slight amount of water in a pH interval of approximately 2 to 7.

EXAMPLE 17

Conversion of 6-β-amino-penicillanic acid-1,1-dioxide into 6,6-bromo- and 6-α-bromo-penicillanic acid-1,1-dioxide with pyridine hydrobromide perbromide and alkyl nitrite and involving 6-diazo-penicillanic acid-1,1-dioxide In the experiments described hereafter, pentyl nitrite was added at 15°–20° C. to a suspension of 6-β-amino-penicillanic acid-1,1-dioxide in an organic solvent followed by about 10 minutes stirring under a nitrogen atmosphere until complete dissolution of the starting material. The solution was cooled to 5° C. followed by introduction of the brominating complex in one portion and stirring for about 30 minutes until TLC indicated complete conversion of 6-diazo-penicillanic acid-1,1-dioxide. As described before, the reaction mixture was treated with a dilute solution of sodium metabisulfite in water and with 4N sodium hydroxide and the organic solvent was removed in vacuo at pH 6–6.5. Except for experiment (a), wherein the mixture of bromides was extracted directly thereafter at pH 2 with ethyl acetate, etc., the solution in water in the other experiments was first purified by two extractions at pH about 6.5 with dichloromethane and the experiments are indicated in the abbreviated form already employed in Examples 8 and 9.

(a) 8 mmol of amino-PAS, 11 mmol of commercial pentyl nitrite, 12 mmol of pyridine hydrobromide perbromide (C$_5$H$_5$N.HBr$_3$) and 20 ml of acetonitrile were reacted to obtain a yield of 2.28 g of good to very good quality. Dibromide:monobromide:ethyl acetate:pentanol ratio was 6:5:1.3:6.6. Maximum yield was 68.8% not taking into account the amount of water present in the starting material and estimated actual yield was 62 to 64%.

In the PMR spectrum (d$_6$-DMSO), (δ-values in ppm, TMS, 60 Mc), 6-α-bromo-penicillanic acid-1,1-dioxide and 6,6-dibromo-penicillanic acid-1,1-dioxide revealed themselves by the following absorption signals.

6-α-bromide: C(CH$_3$)$_2$: 1.41 (s) and 1.51 (s), C$_3$—H: 4.50; C$_5$—H and C$_6$—H about 5.6 (narrow AB quartet, small chemical shift difference, characteristic small J$_{56}$ of trans orientation).

6,6-dibromide: C(CH$_3$)$_2$: 1.41 (s) and 1.51 (s), (complete coincidence with corresponding signals of the 6-α-monobromide); C$_3$—H: 4.68 (S); C$_5$—H: 6.00 (s).

(b) Experiment (a) was repeated with 20 ml of ethyl acetate instead of 20 ml of acetonitrile to obtain a yield of 2.02 g of good to very good quality. Dibromide:-monobromide:ethyl acetate ratio was 2:7:7.5. Maximum yield was 62.7% and estimated actual yield was 56 to 59%.

(c) 8 mmol of amino-PAS, 11 mmol of pentyl nitrite, 25 mmol of the hydrobromide of pyridine (no bromide added) and 20 ml of acetonitrile were reacted and according to TLC, addition of pyridine. HBr to the in situ formed 6-diazo-derivative did not result in noticeable formation of useful products.

(d) 8 mmol of amino-PAS, 11 mmol of pentyl nitrite, 8 mmol of pyridine HBr, 8 mmol of pyridine hydrobromide perbromide and 20 ml of acetonitrile were reacted to obtain yield of only 1.11 g.

(e) 8 mmol of amino-PAS, 11 mmol of pentyl nitrite, 24 mmol of pyridine hydrobromide perbromide and 20 ml of acetonitrile were reacted to obtain a yield of 0.93 g.

(f) 8 mmol of amino-PAS, 11 mmol of pentyl nitrite, 12 mmol of pyridine, 12 mmol of bromine (no hydrobromic acid) and 20 ml of acetonitrile were reacted to obtain a yield of only 1.26 g.

Since in the absence of hydrobromic acid, conversion at 5° C. was considerably slower according to TLC, the temperature was allowed to rise to 20° C. 10 minutes after introduction of bromine and conversion was complete about 40 minutes after introduction of bromine. The relatively low yield suggests that it is necessary to use bromine as well as hydrobromic acid and the same experiment with 1-methyl-imidazole instead of pyridine produced only 0.95 g.

EXAMPLE 18

Preparation of a mixture of the pivaloyloxymethyl esters of 6,6-bibromo- and 6-α-bromo-penicillanic acid-1,1-dioxide (a) Preparation of pivaloyloxymethyl 6-α-amino-penicillanic-1,1-dioxide A mixture of 14.84 g (0.144 mmole) of sodium bromide, 17.5 ml (0.121 mmole) of pivaloyloxymethyl chloride and 320 ml of dry methylformamide was stirred at room temperature for 45 minutes and then 41.92 g (0.120 mmole) of the triethylamine salt of 6-β-amino-penicillanic acid-1,1-dioxide were added to the mixture whereupon stirring was continued for 3.5 hours. The reaction mixture was then poured into a well stirred mixture of 3.2 liters of water and crushed ice, 160 g of sodium chloride and 1.6 liters of ethyl acetate followed by addition of 4N sodium hydroxide until the mixture had attained pH 6.5. The layers were separated and the aqueous layer was extracted three times with 400 ml volumes of ethyl acetate at pH 6.5. The combined organic layers were washed three times with 400 ml volumes of iced water and then was stirred in the cold with anhydrous magnesium sulfate for 30 minutes. The salt was removed by filtration whereupon the filtrate was evaporated in vacuo and the residual oil was stirred with 800 ml of diethyl ether whereupon undissolved material was removed by filtration. The filtrate was diluted with 800 ml of n-hexane and diethyl ether was removed from the turbid solution by concentration in vacuo resulting in precipitation of the desired compound as an oil. n-hexane was removed by decantation followed by sequential addition of 200 ml of diethyl ether and 600 ml of n-hexane. After removal in vacuo of diethyl ether, the now semi-solid product was separated from n-hexane by decantation. The solid was shaken with n-hexane followed by decantation of n-hexane and drying in vacuo to constant weight to obtain a yield of 19.6 g (about 45%) of almost pure product according to thin-layer chromatography and the PMR spectrum.

PMR (CDCl$_3$, 60 Mc, δ-values in ppm TMS): 1.22 (s, 9H), 1.40 (s, 3H), 1.55 (s, 3H), about 2.4 (br, about 2H), 4.48 (s, 1H), about 4.68 to 4.90 (Ab-q with slightly br lines, J=4.5 Hz, 2H) and 5.65 to 6.00 (AB-q, J=5.5 Hz, 2H).

The triethylamine salt of the starting compound can be prepared in high yield as follows: 39,8 g of 6-β-amino-penicillanic acid-1,1-dioxide containing about 6% by weight (equivalent to about 0.75 mol %) of water were suspended with stirring in 700 ml of dichloromethane followed by dropwise introduction of 29.7 ml of triethylamine. After nearly complete dissolution, a small amount of insoluble material was removed by filtration and 700 ml of ethyl acetate were added to the filtrate followed by concentration in vacuo to small volume. After addition of 500 ml of ethyl acetate, concentration in vacuo was repeated. Under cooling with ice, a small amount of diethyl ether was added with stirring or scratching to the almost oily residue. The resulting crystalline mass was transferred to a glass filter, vacuum filtered, washed only with a small amount of diethyl ether and dried in vacuo to obtain a yield of 50 g or more of pure slightly hygroscopic product (has to be stored in the refrigerator). This salt has freely soluble in water and in many commonly employed organic solvents.

(b) Preparation of a mixture of the pivaloyloxymethyl esters of 6,6-dibromo- and 6-α-bromo-penicillanic acid-1,1-dioxide 10.00 g (31.25 mmol) of pyridine hydrobromide perbromide (C$_5$H$_5$H.HBr$_3$) were added under a nitrogen atmosphere and with cooling in an ice bath to a solution of 9.05 g (25 mmol) of the under (a) prepared ester in 62.5 ml of acetonitrile and at a temperature of at most 8° C., 3.75 ml of pentyl nitrite were added dropwise. After about 1 hour, when the evolution of gas had come to a complete stop and the temperature had dropped to about 3° C., 3 ml of pyridine (37 mmol) were introduced slowly. With the help of 50 ml of cold ethyl acetate, the contents of the reaction vessel were transferred into an evaporation flask followed by introduction with shaking of a cold solution of 2.5 g of sodium metabisulfite in 25 ml of water. Organic solvent was removed quickly by evaporation in vacuo in the cold and the solution in water was extracted with 300 ml of diethyl ether whereupon the organic phase was washed three times with 25 ml volumes of iced water. After drying over magnesium sulfate, the solution in diethyl ether was evaporated to a red oil and the product was dissolved in a small volume of dichloromethane and submitted to chromatography through a short silica column. After elution with dichloromethane according to TLC pure and nearly pure fractions were combined, and evaporated in vacuo and the oily, only slightly colored residue was dissolved in 100 ml of diethyl ether followed by addition of 200 ml of n-hexane and concentration in vacuo to a volume of about 80 ml resulting in the precipitation of a semi-solid product. n-hexane was removed by decantation, followed by trituration with a small volume of n-hexane and decantation (two times). After extensive drying in vacuo, the yield was 6.61 g and according to the PMR-spectrum, the product had a purity of 90–95%. It was an approximately 2:1 mixture of 6,6-dibromide and 6-$\alpha$-bromide so that the yield was approximately 55%.

PMR (CDCl$_3$, 60 Mc $\delta$-values in ppm, TMS): 1.22 (s, 9H), 1.43 (s, 3H), 1.59 (s, 3H), 4.43 (s, $\frac{1}{3}$H), 4.52 (s, $\frac{2}{3}$H), 4.69 (d, J=1.5 Hz, $\frac{1}{3}$H); 5.02 (s, $\frac{2}{3}$H), 5.16 (d, J=1.5 Hz, $\frac{1}{3}$H), 5.68 to 6.01 (AB-q, J=5.3H, 2H).

EXAMPLE 19

Preparation of pivaloyloxymethyl 6-diazo-penicillanate-1,1-dioxide and of pivaloyloxymethyl 6-$\alpha$-bromo-penicillanate-1,1-dioxide 1.45 g (4 mmol) of pivaloyloxymethyl 6-$\beta$-amino-penicillanate-1,1-dioxide prepared according to Example 21(a) were dissolved in 15 ml dry acetonitrile and 150 ml of (1.67 mmol) of anhydrous oxalic acid and 0.75 ml (5.5 mmol) of pentyl nitrite were introduced in succession under a nitrogen atmosphere and with stirring at 10° C. The mixture was stirred at 10° C. for 1 hour, followed by fast removal of aolvent in vacuo and dissolution of the residue in about 25 ml of dichloromethane. It was indicated by TLC (silica, diethyl ether—n-hexane) that a virtually quantitative conversion had been reached and this solution was stored overnight at −15° C. A precipitate (a small amount of oxalic acid) was removed by filtration through glass and the filtrate was cooled down to below −10° C., and then was washed twice with 8 ml volumes of sodium chloride containing water of −10° to −15° C. While still cold, the solution was stored over anhydrous magnesium sulfate with occasional shaking at −15° C. for 1 hour and the salt was removed by filtration and washed with small volumes of cold dichloromethane. The combined filtrate was evaporated in vacuo to a semi-solid, partially crystalline residue and the residue was triturated with cold n-hexane and then stored for 2 hours at −15° C. The now completely solid and largely crystalline product was collected by filtration, washed with a cold 1:1 mixture of n-hexane and carbon tetrachloride and subsequently dried extensively in vacuo to obtain a yield of 1.2 g of an about 80% pure product.

IR (KBr-disc, values in cm$^{-1}$): among other absorptions 2980 (m), 2135 (m), 1775 (s), 1755 (vs), 1330 (s), 1120 (s).

PMR (CDCl$_3$, 60 Mc, $\delta$-values in ppm, TMS): 1.23 (s, 9H), 1.43 (s, 3H), 1.58 (s, 3H), 5.65 to 5.98 (AB-q, J about 6.0 cps, 2H), 4.24 (s, 1H) and 5.47 (s, 1H).

(b) Preparation of pivaloyloxymethyl 6-$\alpha$-bromo-penicillanate-1,1-dioxide 1.28 g (4 mmol) of pyridine hydrobromide perbromide was added at 0°–5° C. in portions over 10 minutes to a stirred solution of 1.1 g of the above prepared crude diazo-derivative in 10 ml of dry acetonitrile and the ice-bath was then removed and the solution was allowed to reach room temperature (about 20° C.) followed by 10 minutes additional stirring. TLC (silica, 2:1 mixture of diethyl ether and n-hexane) indicated complete conversion of the diazo-derivative and 0.4 ml of pyridine and a solution of 0.4 g of sodium metabisulfite in 4 ml of water were added sequentially with cooling. Acetonitrile was removed by concentration in vacuo whereupon the remaining mixture was extracted three times with about 12 ml volumes of diethyl ether. The combined extract was washed with a saturated sodium chloride solution in water, dried over anhydrous magnesium sulfate, filtered and evaporated in vacuo. The residue was dissolved in a small volume of dichloromethane, and the solution was submitted to chromatography through a short column of silica with dichloromethane as eluant to obtain a yield of 0.9 g of almost pure pivaloyloxymethyl 6-$\alpha$-bromo-penicillanate-1,1-dioxide. The presence of the 6,6-dibromide was not noticeable in the PMR spectrum.

EXAMPLE 20

Preparation of pivaloyloxymethyl 6,6-dibromo-penicillanate-1,1-dioxide

The diazotization was performed as described in Example 19 starting with 2.9 g (8 mmol) of pivaloyloxymethyl 6-$\beta$-amino-penicillanate-1,1-dioxide and 360 mg (4 mmol) of oxalic acid, 1.5 ml (11 mmol) of pentyl nitrite and 15 ml of acetonitrile. After complete conversion of the starting material, 3.84 g (12 mmol) of pyridinium hydrobromide perbromide were added as described in Example 19 and after complete conversion, 1 ml of pyridine and a solution of 1 g of sodium metabisulfite were added sequentially. Acetonitrile was removed in vacuo, and the remaining mixture was three times extracted with 30 ml volumes of diethyl ether, etc. The crude product was submitted to column chromatography as described in Example 19 to obtain a yield of 1.92 g of, according to the PMR spectrum, almost pure pivaloyloxymethyl 6,6-dibromo-penicillanate-1,1-dioxide. The final product contained about 5 mol % of one unknown by product and the corresponding 6-$\alpha$-monobromide was not present according to the PMR spectrum.

EXAMPLE 21

Preparation of crude mixtures of 6,6-dibromopenicillanic acid-1,1-dioxide and 6-$\alpha$-penicillanic acid-1,1-dioxide with variations in reactane and auxiliary agents HBr was added as a 47% solution to a stirred and cooled (0° to 5° C.) suspension of APZ-sulfone in acetonitrile which resulted in a clear solution and then the auxiliary agent and bromine were added to the above solution followed by portionwise addition of sodium nitrite over a period of 15 minutes while keeping the temperature between 0° to 5° C. The resulting contents were further stirred for 30 minutes at 0° to 5° C. and then sodium metasulfite solution was added so that temperature does not exceed 5° C. Then, with 1N NaOH, the pH was raised to 5.5 and acetonitrile was removed under reduced pressure (waterpump). The resulting solution was brought to pH 6.5 with 4N NaOH and extracted with dichloromethane. The aqueous layer was then brought to a pH of 2 with 4N HCl and was extracted three times with ethyl acetate. The combined ethyl acetate extracts were dried over MgSO$_4$ and solvent was removed under reduced pressure. The product was dried over P$_2$O$_5$ under reduced pressure and weighed (noted in the table I as yield in g). The said process was varied as indicated in Table A.

penicillanic acid-1,1-dioxide are obtained in very attractive yields by the process of the invention.

EXAMPLE 22

Diazotization/bromination of 6-β-amino-penicillanic acid-1,1-dioxide without an auxiliary reagent using sodium nitrite as the diazotization reagent 7.9 ml of a solution of HBr (68.75 mmol) in water were added at 0° to 5° C. to a stirred suspension of 6.2 g (purity by HPLC; 91%; 22.75 mmole) of APZ-sulfone

TABLE A

Example 21 - Experiments a–n

| Exp. | HBr mmol | Amino PAS mmol | Br$_2$ | Nitrite mmol | Acetonitile ml | Auxiliary agent |
|---|---|---|---|---|---|---|
| a | 22 | 8 | 12 | 9.5 NaNO$_2$ | 25 | 12 mmol 4-methyl-pyrimidine |
| b | 22 | 8 | 12 | 9.5 NaNO$_2$ | 25 | 0.8 mmol 4-methyl-pyrimidine |
| c | 22 | 8 | 12 | 9.5 NaNO$_2$ | 25 | 0.8 mmol caprolactam |
| d | 220 | 80 | 120 | 95 NaNO$_2$ | 250 | 8 mmol caprolactam |
| e | 22 | 8 | 12 | 9.5 NaNO$_2$ | 25 | 0.8 mmol N—vinyl-imidazole |
| f | 110 | 40 | 12 | 47.5 NaNO$_2$ | 125 | 4 mmol N—vinyl-imidazole |
| g | 22 | 8 | 12 | 9.5 NaNO$_2$ | 25 | 0.8 mmol succinimide |
| h | 110 | 40 | 60 | 47.4 NaNO$_2$ | 25 | 4 mmol N—benzyl-benzene-sulfonamide |
| i | 22 | 8 | 12 | 9.5 NaNO$_2$ | 25 | 0.8 mmol 2-dimethylamino-pyridine |
| j | 22 | 8 | 12 | 9.5 NaNO$_2$ | 25 | 0.8 mmol ethylcyanoacetate |
| k | 110 | 40 | 60 | 47.5 NaNO$_2$ | 25 | 0.45 mmol ethylcyanoacetate |
| l | 22 | 8 | 12 | 12 pentyl nitrite | 25 | 0.8 mmol methyl-imidazole |
| m | 22 | 8 | 12 | 11 pentyl nitrite | 25 | 0.8 mmol methyl-imidazole |
| n | 28 | 8 | 12 | 16 pentyl nitrite | 25 | 0.8 mmol pyridine |

The results of the above experiments are given in Table B.

TABLE B

Example 21 - Experiments a–n yields and results of NMR-analysis. Ratio = molar ratio of 6,6-dibromo-penicillanic acid-1,1-dioxide: 6-α-bromo-penicillanic acid-1,1-dioxide

| Experiment | Yield in g | Ratio | Ethyl acetate mol % | Maximum yield % | Estimated actual yield % |
|---|---|---|---|---|---|
| a | 2.2 | 9:7.5 | 11 | 74.5 | 69–72 |
| b | 2.42 | 8:1 | 11 | 76.4 | 70.3 |
| c | 2.36 | 3:1 | 12 | 76 | 68–70 |
| d | 21.61 | 10:75 | 10 | 72.4 | 66.5 |
| e | 2.42 | 13:2 | 14 | 75.4 | 67.9 |
| f | 11.05 | 10:7.5 | 13 | 74.4 | 68 |
| g | 2.44 | 14:3 | 12 | 79.5 | 71.5 |
| h | 11.12 | 11:6.5 | 12 | 73.9 | 66.5 |
| i | 2.48 | 18:2.5 | 10 | 78.9 | 71 |
| j | 2.2 | 1:1 | 14 | 73.4 | 68–71 |
| k | 11.47 | 5:3 | 13 | 75.2 | 67.6 |
| l | 2.40 | 16:1.5 | 12 | 75.3 | 69.7 |
| m | 2.35 | 16:1 | 12 | 73.8 | 66.4 |
| n | 2.37 | 29:3 | 13 | 74.3 | 66 |

In all experiments there was also found a little quantity of unknown products. The experiments of this Example 21 show also that mixtures of 6,6-dibromo-penicillanic acid-1,1-dioxide and 6-α-bromo-penicillanic acid-1,1-dioxide, valuable intermediates for the preparation of in 75 ml of acetonitrile. Thereafter 1.92 ml (37.5 mmol) of bromine were added to the above solution and followed by portionwise addition of sodium nitrite (2.05 g; 29.7 mmol) over a period of 15 minutes while keeping the temperature between 0° to 5° C. The resulting contents were further stirred for 30 minutes at 0° to 5° C. and then sodium metabisulfite solution (3.1 g in 60 ml water) was added so that temperature does not exceed 5° C. Then with 4N NaOH, the pH was raised to 3.5 and acetonitrile was evaporated under reduced pressure (water pump), and the resulting mixture was extracted with ethyl acetate (3×100 ml). The combined ethyl acetate extracts were washed twice with 50 ml of brine, dried over anhydrous magnesium sulfate and solvent was removed under reduced pressure to yield 7.57 g of 6,6-dibromopenicillanic acid-1,1-dioxide and 6-α-bromopenicillanic acid-1,1-dioxide (purity: 6,6-dibromopenicillanic acid-1,1-dioxide: 80.7% and 6-α-bromopenicillanic acid-1,1-dioxide, 7.4%) thus giving a yield of 6,6-dibromopenicillanic acid-1,1-dioxide of 68.7% and 6-α-bromopenicillanic acid-1,1-dioxide of 7.9%. The purity was determined through 60 MHz spectroscopy using maleic acid as the reference.

EXAMPLE 23

Diazotization/bromination of 6-β-amino-penicillanic acid-1,1-dioxide, using an auxiliary reagent and using pentyl nitrite as the diazotization reagent.

With cooling with iced water, 10 g of APZ-sulfone (purity by HPLC 91%; 44.8 mmol) were dissolved with stirring in a 12.5 ml of a solution of hydrobromic acid (110 mmol) in 125 ml of acetonitrile. Continuously operating at 0° to 5° C., there were added subsequently 0.32 ml of 1-methylimidazole (4 mmol) and 3.1 ml of bromine (60 mmol) immediately followed by the introduction of 8 ml of pentylnitrite (60 mmol). After 45 minutes of additional stirring, a solution of 5 g of sodium metabisulfite in 100 ml water and 4N NaOH were added with stirring till the pH reached 6.5. Then acetonitrile was removed by concentration in vacuo, followed by two extractions with 50 ml of dichloromethane. The remaining solution in water was extracted three times at pH 3.5 with 100 ml of ethyl acetate. The combined extracts were twice washed with a small volume of brine, dried over anhydrous magnesium sulfate and solvent removed under reduced pressure to yield 11.16 g of 6,6-dibromopenicillanic acid-1,1-dioxide and 6-α-bromopenicillanic acid-1,1-dioxide (purity: 6,6-dibromopenicillanic acid-1,1-dioxide: 76.3% and 6-α-bromopenicillanic acid-1,1-dioxide: 11.1%), thus giving a yield of 6,6-dibromopenicillanic acid-1,1-dioxide of 59% and 6-α-bromopenicillanic acid-1,1-dioxide of 10.8%. The purity was determined through 60 MHz spectroscopy using maleic acid as the reference.

EXAMPLE 24

Diazotization/bromination of 6-β-amino-penicillanic acid-1,1-dioxide without an auxiliary reagent using pentyl nitrite as the diazotization reagent With cooling with iced water, 10 g of APZ-sulfone (purity by HPLC 91%; 44.8 mmol) were dissolved with stirring in a 12.5 ml of a solution of hydrobromic acid (110 mmol) in 125 ml of acetonitrile. Continuously operating at 0° to 5° C., there was added 3.1 ml of bromine (60 mmol) immediately followed by the introduction of 8 ml of pentyl nitrite (60 mmol). After 45 minutes of additional stirring, a solution of 5 g of sodium metabisulfite in 100 ml water and 4N NaOH were added with stirring till pH raised to 3.5 and acetonitrile was removed under reduced pressure followed by extraction three times with 100 ml of ethyl acetate. The combined extracts were twice washed with a small volume of brine, dried over anhydrous magnesium sulfate and solvent removed under reduced pressure to yield 12.2 g of 6,6-dibromopenicillanic acid-1,1-dioxide and 6-α-bromopenicillanic acid-1,1-dioxide (purity: 6,6-dibromopenicillanic acid-1,1-dioxide: 74.4 and 6-α-brompenicillanic acid-1,1-dioxide: 9.3% thus giving a yield· of 6,6-dibromopenicillanic acid-1,1-dioxide of 63% and 6-α-bromopenicillanic acid-1,1-dioxide of 9.9%. The purity was determined through 60 MHz spectroscopy using maleic acid as reference.

EXAMPLE 25

Example 22 was repeated were 12.5 ml of hydrogen bromide solution (39 mmol) in water and 3.3 ml of 12N sulfuric acid (20 mmol) to obtain 6.06 g of product with a purity of 64.2% of 6,6-dibromo-penicillanic acid-1,1-dioxide and 26.0% of 6-α-bromo-penicillanic acid-1,1-dioxide for a yield of 44.3% of 6,6-dibromo-penicillanic acid-1,1-dioxide and 22.5% of 6-α-bromo-penicillanic acid-1,1-dioxide.

Various modifications of the product and process of the invention may be made without departing from the spirit or scope thereof and it is to be understood that the invention is intended to be limited only as described in the appened claims.

What we claim is:

1. A process for the preparation of at lease one compound of a formula selected from the group consisting of

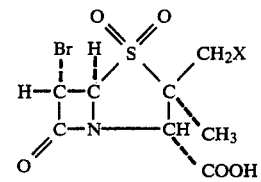

and

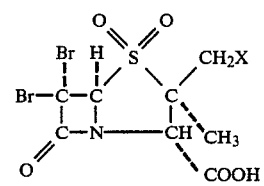

and their pharmaceutically acceptable salts and esters wherein X is selected from the group consisting of hydrogen and chlorine and acetoxy comprising diazotizing a compound of the formula

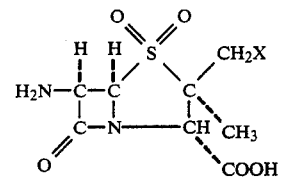

and pharmaceutically acceptable salts and esters thereof wherein X has the above definition with at least an equimolar amount of a nitrosating agent in the presence of 1 to 5 equivalents of a strong acid in solution or suspension in a mixture of water and an at least partially water-miscible organic solvent with the amount of water being 1 to 20% by volume and brominating the resulting diazotized compound with at least equimolar amounts of hydrogen bromide and bromine.

2. The process of claim 1 wherein the reaction is performed at a temperature between −20° and 30° C.

3. The process of claim 1 wherein the reaction is performed at a temperature between −10° and 15° C.

4. The process of claim 1 wherein the strong acid is an aryl sulfonic acid aryl bisulfonic acid, sulfuric acid and hydrobromic acid.

5. The process of claim 1 wherein the organic solvent medium is selected from the group consisting of acetonitrile, 1,2-dimethoxy-ethane, ethyl acetate, methyl acetate, nitromethane, tetrahydrofuran and 1,4-dioxane and a mixture of two solvents consisting of at least 80% by volume of acetonitrile, ethyl acetate or dichloromethane with at most 20% by volume of sulfolane, dimethyl sulfoxide, 1,1,3,3-tetramethyl-urea, dicyanomethane, a lower alkyl cyanoacetate or a di(lower)alkyl malonate.

6. The process of claim 1 wherein the organic solvent is acetonitrile or 1,2-dimethoxyethane.

7. The process of claim 1 wherein the organic solvent medium is a mixture of acetonitrile or ethyl acetate with dicyanomethane or methyl cyanoacetate or ethyl cyanoacetate or dimethyl malonate or diethyl malonate.

8. The process of claim 1 wherein the nitrosating agent used is selected from the group consisting of sodium nitrite, potassium nitrite, ethyl nitrite, 1-pentyl-nitrite, 2-pentyl-nitrite and a commercially available mixture of 1-pentyl-nitrite and 2-pentyl-nitrite.

9. The process of claim 8 wherein the nitrosating agent is selected from the group consisting of sodium nitrite and a commercially available mixture of 1-pentyl-nitrite and 2-pentyl-nitrile.

10. The process of claim 1 wherein an auxiliary agent is used to facilitate the bromination of the diazotized 6-amino-penicillanic acid derivative.

11. The process of claim 10 wherein the auxiliary agent is selected from the group consisting of (a) tertiary (cyclo)aliphatic amines having attached to the nitrogen atom three groups selected from straight- and chain-alkyl groups containing up to 6 carbon atoms and from saturated 5 to 7 membered cycloalkyl groups; (b) tertiary saturated 5 to 7 membered heterocyclic amines, the ring nitrogen atom being further attached to a (cyclo)alkyl group as defined above, while the ring may also contain one oxygen atom or one additional nitrogen atom carrying a (cyclo)alkyl group as defined above, (c) tertiary, fully unsaturated heterocyclic amines selected from the group consisting of pyridine, quinoline, isoquinoline, pyrimidine, pyrazine, N-(cyclo)alkyl-imidazole, N-vinyl-imidazole and the (cyclo)alkyl groups as defined above; (d) pyridine-1-oxides; (e) sulfones and sulfoxides having attached to the sulfur atom two optionally substituted groups selected from the group consisting of alkyl, cycloalkyl arylmethyl, arylethyl or a trimethylene, a tetramethylene or a pentamethylene unit, with for aryl, phenyl, biphenyl, 1- or 2-naphthyl and pyridyl and the (cyclo)alkyl groups as defined above; (f) alkyl, cycloalkyl, arylmethyl, arylethyl and aryl carbonamides, as well as N-mono (cyclo)alkyl and N-monoaryl derivatives thereof, the (cyclo)alkyl and the aryl groups as defined above; (g) saturated, monocyclic, 5 to 7 membered lactams; (h) alkyl, (cyclo)alkyl, arylmethyl, arylethyl and arylsulfonamides, as well as N-mono (cyclo)alkyl and N-mono-aryl derivatives thereof, the (cyclo)alkyl and the aryl groups as defined above; (i) N-monoacylureides of the formula Q-CO-NH-CO-NH-Q$^1$ wherein Q is selected from the group consisting of a (cyclo)alkyl, arylmethyl, arylethyl and aryl with the aryl and the (cyclo)alkyl as defined above and Q$^1$ is selected from the group consisting of hydrogen and (cyclo)alkyl as defined above, Q and Q$^1$ together form a saturated 5- to 6-membered ring in the methylene or ethylene unit optionally substituted with two methyl groups or one phenyl group, (j) imides of the formula Q$^2$—CO—NH—CO—Q$^3$, wherein Q$^2$ and Q$^3$ are selected from the group consisting of (cyclo)alkyl, arylmethyl, arylethyl or aryl groups with aryl and (cyclo)alkyl as defined above, and Q$^2$ and Q$^3$ together form a saturated 5- to 6-membered ring optionally substituted in the ethylene or propylene unit by one or two methyl groups or one phenyl; (k) disulfonylamines of the formula aryl —SO$_2$—NH—SO$_2$—aryl with aryl the same or different and defined as above; (l) composite imides of the type aryl —SO$_2$—NH—CO—Q$^4$, wherein Q$^4$ is aryl or (cyclo)alkyl, with aryl groups and the (cyclo)alkyl groups as defined above; (m) phthalimide and saccharine; (n) guanidine, and guanidines carrying up to four lower alkyl groups, having a C=N—H fragment, with lower alkyl as defined before; (o) non-hydroxylic derivatives of malonic acid in which the carboxyl groups are replaced by two cyano, and/or N,N-di(lower)alkyl-carbamoyl and/or (lower)alkoxycarbonyl groups, optionally substituted in the methylene group by a lower alkyl group, and (p) α,ω-dicyanoalkanes.

12. The process of claim 1 wherein X is hydrogen.

13. The process of claim 1 wherein 6,6-dibromo-penicillanic acid-1,1-dioxide is obtained using an auxiliary agent selected from the group consisting of pyridine, sulfolane, hydantoin, phenylacetyl urea, p-tolyl-sulfonamide, succinimide, diphenyl sulfoxide, dimethyl-sulfone and 1-vinyl-imidazole.

14. The process of claim 1 wherein 6-α-bromo-penicillanic acid-1,1-dioxide is obtained using an auxiliary agent selected from the group consisting of 2-dimethylamino-pyridine, 4-dimethylamino-pyridine and 1-methyl-imidazole.

15. The process of claim 1 comprising nitrosating a 6-amino-penicillanic acid-1,1-dioxide derivative of the formula

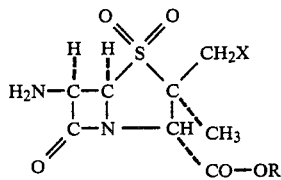

wherein X is as defined in claim 1, and R is hydrogen, a metal or an ester in solution or suspension in a non-hydroxyl inert organic solvent medium containing up to 10% by weight of water with an at least equimolar amount of an alkyl nitrite or cycloalkyl nitrite to form a 6-diazo-penicillanic acid-1,1-dioxide of the formula

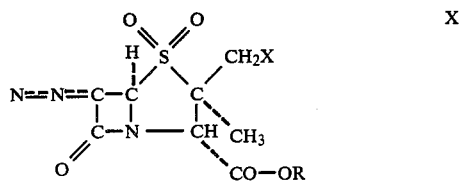

wherein X and R are as defined above, optionally isolating from the reaction mixture the said diazo compound as such or when R is hydrogen—as a salt, converting the diazo compound into a 6-α-bromo- and/or 6,6-dibromo-penicillanic acid-1,1-dioxide derivative of the formula I and/or II or ester thereof by the addition of a complex or a mixture containing at least equimolar amounts of bromine and hydrogen bromide and optionally a tertiary amine.

16. The process of claim 15 wherein the reaction is performed at a temperature between −20° and 30° C.

17. The process of claim 15 wherein the reaction is performed at a temperature between −10° and 15° C.

18. The process of claim 17 wherein R is hydrogen and the nitrosation step is carried out with no added water and in the absence of bromine and hydrogen bromide.

19. The process of claim 17 wherein R is an ester residue and the nitrosation step is carried out in the presence of a mixture of bromine, hydrogen bromide and a tertary amine.

20. The process of claim 19 wherein the reaction steps are effected in a non-hydroxyl inert organic solvent in the presence of up to an equimolar amount of a water-soluble carboxylic acid having a $pK_a$-value in water of 1.5 to 5.0.

21. The process of claim 17 wherein R is selected from the group consisting of 3-phthalidyl and alkylcarbonyloxymethylene optionally substituted on the methylene group by one or two methyl groups and the alkyl group contains 1 to 5 carbon atoms.

* * * * *